(12) United States Patent
Nakamura et al.

(10) Patent No.: US 7,939,254 B2
(45) Date of Patent: May 10, 2011

(54) BREAST CANCER RELATED GENE ZNFN3A1

(75) Inventors: Yusuke Nakamura, Bunkyo-ku (JP);
Yoichi Furukawa, Bunkyo-ku (JP);
Shuichi Nakatsuru, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 155 days.

(21) Appl. No.: 11/817,303

(22) PCT Filed: Feb. 9, 2006

(86) PCT No.: PCT/JP2006/302683
§ 371 (c)(1),
(2), (4) Date: Jan. 12, 2009

(87) PCT Pub. No.: WO2006/092958
PCT Pub. Date: Sep. 8, 2006

(65) Prior Publication Data
US 2009/0142344 A1 Jun. 4, 2009

Related U.S. Application Data

(60) Provisional application No. 60/657,581, filed on Feb. 28, 2005.

(51) Int. Cl.
*C12Q 1/68* (2006.01)
*G01N 33/53* (2006.01)

(52) U.S. Cl. ............................................. 435/6; 435/7.1

(58) Field of Classification Search ........................ None
See application file for complete search history.

(56) References Cited

U.S. PATENT DOCUMENTS

| 2004/0235018 | A1 | 11/2004 | Nakamura et al. |
| 2009/0035303 | A1 | 2/2009 | Nakamura et al. |
| 2009/0191181 | A1 | 7/2009 | Nakamura et al. |
| 2010/0184088 | A1 | 7/2010 | Nakatsuru |
| 2010/0248240 | A1 | 9/2010 | Nakamura et al. |

FOREIGN PATENT DOCUMENTS

| JP | 2004/264294 A | 9/2004 |
| JP | 2005-511023 T | 4/2005 |
| WO | WO 00/17355 A2 | 3/2000 |
| WO | WO 00/44900 A2 | 8/2000 |
| WO | WO 02/059377 A2 | 8/2002 |
| WO | WO 02/090578 A2 | 11/2002 |
| WO | WO 02/092002 A2 | 11/2002 |
| WO | WO 03/010180 A1 | 2/2003 |
| WO | WO 03/027143 A2 * | 4/2003 |
| WO | WO 2004/076623 A2 | 9/2004 |
| WO | WO 2005/071102 A2 | 8/2005 |
| WO | WO 2008/152816 A1 | 12/2008 |

OTHER PUBLICATIONS

Hamamoto et al (Proceedings of the 93rd Annual Meeting of the American Association for Cancer Research, 2002, p. 13, Abstract 63).*

Firestein, R., et al., "Set Domain-Dependent Regulation of Transcriptional Silencing and Growth Control by SUV39H1, a Mammalian Ortholog of Drosophila Su(var)3-9," *Molecular and Cellular Biology*, vol. 20(7), pp. 4900-4909 (Jul. 2000).

Fu, T-B, et al., "The RNAs of Hepatitis Delta Virus Are Copied by RNA Polymerase II in Nuclear Homogenates," *Journal of Virology*, vol. 67(12), pp. 6965-6972 (Dec. 1993).

Hamamoto, et al., "Isolation and characterization of ZNFN3A1, a novel gene whose expression is frequently up-regulated in hepatocellular carcinoma," *Jpn J Cancer Res* (Proceeding Sixtieth Annual Meeting of the Japanese Cancer Association), vol. 92 (Supplement), p. 117, abstract 208 (2001).

Kato, T. et al., "Isolation of a novel human gene, DDEFL1 (Development and Differentiation Enhancing Factor-Like 1), as a molecular target of HCC," *Jpn J Cancer Res* (Proceedings Sixty-First Annual Meeting of the Japanese Cancer Association), vol. 93 (Supplement), p. 78, abstract 2033 (2002).

Luking, et al., "The Protein Family of RNA Helicases," *Crit Rev Biochem Mol Biol.*, vol. 33(4), pp. 259-296 (1998).

Mao, Y., et al., Geneseq Accession No. AAG66728, 1 pp (Nov. 26, 2001).

Nakajima, T., et al., "RNA Helicase A Mediates Association of CBP with RNA Polymerase II," *Cell*, vol. 90(6), pp. 1107-1112 (Sep. 19, 1997).

Nozaki, T., et al., "Involvement of the VEGFR-1 in prostatic carcinogenesis," *The American Association for Cancer Research/AACR*, vol. 45, p. 213, abstract #934 (2004).

Okabe, H., et al., "Genome-wide Analysis of Gene Expression in Human Hepatocellular Carcinomas Using cDNA Microarray: Identification of Genes Involved in Viral Carcinogenesis and Tumor Progression," *Cancer Research*, vol. 61(5), pp. 2129-2137 (Mar. 1, 2001).

Rea, S., et al., "Regulation of chromatin structure by site-specific histone H3 methyltransferases," *Nature*, vol. 406(6796), pp. 593-599 (Aug. 10, 2000).

Rozovskaia, T., et al., "Self-association of the SET domains of human ALL-1 and of Drosophila TRITHORAX and ASH1 proteins," *Oncogene*, vol. 19(3), pp. 351-357 (Jan. 20, 2000).

Shibuya, M., et al., "Differential Roles of Vascular Endothelial Growth Factor Receptor-1 and Receptor-2 in Angiogenesis," *Journal of Biochemistry and Molecular Biology*, vol. 39(5), pp. 469-478 (Sep. 30, 2006).

(Continued)

*Primary Examiner* — Sean E Aeder

(74) *Attorney, Agent, or Firm* — Kilpatrick Townsend & Stockton LLP

(57) ABSTRACT

Objective methods for detecting and diagnosing breast cancer (BRC) are described herein. Also described are methods of treating and preventing breast cancer and breast cancer metastasis as well as methods of assessing the prognosis of a breast cancer subject and the efficacy of a breast cancer therapy. In one embodiment, the diagnostic method involves determining the expression level of ZNFN3A1, a gene whose expression is markedly elevated in breast cancers, that therefore can be used to discriminate between BRC cells and normal cells. The present invention further provides methods of screening for therapeutic agents useful in the treatment of BRC, methods of treating BRC and method for vaccinating a subject against BRC.

7 Claims, 4 Drawing Sheets

OTHER PUBLICATIONS

Stockand, J., et al., "S-Adenosyl-$_L$-homocysteine Hydrolase Regulates Aldosterone-induced Na$^+$Transport," *The Journal of Biological Chemistry*, vol. 274(6), pp. 3842-3850 (Feb. 5, 1999).

Strahl, B., et al., "Methylation of histone H3 at lysine 4 is highly conserved and correlates with transcriptionally active nuclei in *Tetrahymena*," *PNAS*, vol. 96(26), pp. 14967-14972 (Dec. 21, 1999).

Strausberg, R. et al., "Generation and initial analysis of more than 15,000 full-length human and mouse cDNA sequences," *PNAS*, vol. 99(26), pp. 16899-16903 (Dec. 24, 2002 Epub Dec. 11, 2002).

Strausberg, R., et al., "Homo sapiens SET and MYND domain containing 3, mRNA (cDNA clone MGC:32757 IMAGE:4334047), complete cds," GenBank Accession No. BC031010, 3 pgs. (Jun. 13, 2002).

Database EMBL Accession No. AK024733; Sep. 29, 2000. Sugano, Sumio, et al.

Database EMBL Accession No. AL557360; Feb. 11, 2001. Genescope.

Database Geneseq refSN: ID: rs 10672134; Nov. 13, 2003. (Update Nov. 22, 2003).

Database GeneCards "GeneCard for protein-coding SMYD3 GC01M242239 [abstract]"; Reference XP-002385380 Xennex Inc.; "SMYD3" retrieved from http://www.genecards.org/cgi-bin/card-disp.pl?gene=smyd3&search=smyd3&suff=txt, 2008.

Du, Yong, et al., "Hypermethylation in human cancers of the RIZ1 tumor suppressor gene, a member of a histone/protein methyltransferase superfamily," 2001, *Cancer Research*, vol. 61 (22), pp. 8094-8099.

Echeverri, Chris, et al, "siRNA design: It's all in the algorithm," 2004, Ambion TechNotes, vol. 11(3), from Ambion.com.

Furukawa, Yoichi, et al., "*SMYD3* encodes a novel histone methyltransferase involved in human carcinogenesis [abstract]." Jul. 22-24, 2005; Tokyo, Japan. In: imsut LOCUS Newsletter; System Genome Medicine—Bench to Bedside—Shirokane International Symposium; No. 3, Jul. 2005; p. 12, Session 1.

Hamamoto, Ryuji, et al., "*ZNFN3A1*, a novel gene that promotes growth in hepatocellular carcinoma [abstract]." In: Proceedings of the 93rd Annual Meeting of the American Association for Cancer Research. Apr. 6-10, 2002; San Francisco, CA. Philadelphia (AP): AACR; 2002. p. 13. Abstract No. 63.

Hamamoto, Ryuji, et al., "*SMYD3* encodes a histone methyltransferase involved in the proliferation of cancer cells," 2004, *Nature Cell Biology*, vol. 6(8), pp. 731-740.

Hamamoto, Ryuji, et al., *SMYD3* encodes a novel histone methyltransferase involved in the proliferation of cancer cells through a transcriptional regulation [abstract + presentation].: In: Proceedings of the 96th Annual Meeting of the American Association for Cancer Research. Apr. 16-20, 2005; Anaheim, CA. Philadelphia (AP): AACR; 2005. vol. 46, p. 648. Abstract No. 2754.

Hamamoto, Ryuji, et al., "Enhanced SMYD3 expression is essential for the growth of breast cancer cells," 2006, *Cancer Sci.*, vol. 97(2), pp. 113-118.

Tsuge, Masataka, et al., "A variable number of tandem repeats polymorphism in an E2F-1 binding element in the 5' flanking region of *SMYD3* is a risk factor for human cancers," 2005, *Nature Genetics*, vol. 37(10), pp. 1104-1107.

* cited by examiner a b a b

BREAST CANCER RELATED GENE ZNFN3A1

CROSS-REFERENCES TO RELATED APPLICATIONS

This application is a U.S. National Stage Application of PCT/JP2006/302683, filed Feb. 9, 2006, which claims the benefit of U.S. Provisional Application Ser. No. 60/657,581 filed Feb. 28, 2005, all of which are hereby incorporated by reference in their entirety.

TECHNICAL FIELD

The present invention relates to methods of detecting and diagnosing breast cancer as well as methods of treating and preventing breast cancer and breast cancer metastasis.

BACKGROUND OF THE INVENTION

Breast cancer (BRC), a genetically heterogeneous disease, is the most common malignancy in women. An estimated 800,000 new cases are reported each year worldwide (Parkin D M. et al., (1999) C A Cancer J Clin 49: 33-64). Mastectomy is currently the primary treatment option for this disease. However, even with surgical removal of the primary tumor(s), relapse at local or distant sites may occur due to undetectable micrometastases (Saphner T. et al., (1996) J Clin Oncol 14, 2738-2749) present at the time of diagnosis. Cytotoxic agents are usually administered as adjuvant therapy after surgery to kill those residual or premalignant cells.

Treatment with conventional chemotherapeutic agents is often empirical and is mostly based on histological tumor parameters, and in the absence of specific mechanistic understanding. Target-directed drugs are therefore becoming the bedrock treatment for BRC. Tamoxifen and aromatase inhibitors, two representatives of its kind, have been achieved great responses when used as adjuvant or chemoprevention in patients with metastasized BRC (Fisher B. et al., (1998) J Natl Cancer Inst 90, 1371-88; Cuzick J (2002) Lancet 360, 817-24). However, the drawback is that only patients' expressed estrogen receptors are sensitive to these drugs. Furthermore, recent concerns raised regarding their side effects particularly focused on the possibility that long term tamoxifen treatment may cause endometrial cancer as well as the deleterious effects of bone fractures in postmenopausal women treated with aromatase (Coleman R E (2004) Oncology. 18 (5 Suppl 3), 16-20). Due to the emergence of side effect and drug resistance, the search and identification of novel molecular targets for selective smart drugs on the basis of characterized mechanisms of action is now necessary.

BRC is a complex disease associated with numerous genetic changes. Little is known about whether these abnormalities are the cause of breast tumorigenesis, although it has been reported that they occur by a multistep process which can be broadly equated to transformation of normal cells, via the steps of atypical ductal hyperplasia, ductal carcinoma in situ (DCIS) and invasive ductal carcinoma (IDC). There is evidence that only a portion of premalignant lesions are committed to progression to invasive cancer while the other lesions undergo spontaneous regression. This explanation of molecular participation, which leads to development of primary BRC, its progression, and its formation of metastases, is the main focus for new strategies targeted at prevention and treatment.

Gene-expression profiles generated by cDNA microarray analysis can provide considerably more detail about the nature of individual cancers than traditional histopathological methods are able to supply. The promise of such information lies in its potential for improving clinical strategies for treating neoplastic diseases and developing novel drugs (Petricoin, E. F. et al., (2002) Nat Genet, 32 Suppl. 474-9.). To this aim, the present inventors have analyzed the expression profiles of tumor(s) from various tissues using cDNA microarrays (Okabe, H. et al., (2001) Cancer Res, 61: 2129-37.; Hasegawa, S. et al., (2002) Cancer Res, 62: 7012-7.; Kaneta, Y. et al., (2002) Jpn J Cancer Res, 93: 849-56.; Kaneta, Y. et al., (2003) Int J Oncol, 23: 681-91.; Kitahara, 0. et al., (2001) Cancer Res, 61: 3544-9.; Lin, Y. et al. (2002) Oncogene, 21: 4120-8.; Nagayama, S. et al., (2002) Cancer Res, 62: 5859-66.; Okutsu, J. et al., (2002) Mol Cancer Ther, 1: 1035-42.; Kikuchi, T. et al., (2003) Oncogene, 22: 2192-205.).

Recent examination into the expression levels of thousands of genes through the use of cDNA microarrays have resulted in the discovery of distinct patterns in different types of BRC (Sgroi, D. C. et al., (1999) Cancer Res, 59: 5656-61.; Sorlie, T. et al., (2001) Proc Natl Acad Sci U S A, 98: 10869-74.; Kauraniemi, P. et al., (2001) Cancer Res, 61: 8235-40.; Gruvberger, S. et al., (2001) S. Cancer Res, 61: 5979-84.; Dressman, M. et al., (2003) Cancer Res, 63: 2194-2199.).

Previous studies into gene-expression profiles in BRCs have resulted in the identification of genes that may serve as candidates for diagnostic markers and/or prognosis profiles. However, these data, derived primarily from tumor masses, do not adequately reflect the expressional changes that arise during breast carcinogenesis, because BRC cells exist as a solid mass with a highly inflammatory reaction and containing various cellular components. Therefore, previously published microarray data is likely to reflect heterogenous profiles.

Studies designed to reveal mechanisms of carcinogenesis have already facilitated the identification of molecular targets for certain anti-tumor agents. For example, inhibitors of farnesyltransferase (FTIs), which were originally developed to inhibit the growth-signaling pathway related to Ras, whose activation depends on post-translational farnesylation, have been shown to be effective in treating Ras-dependent tumors in animal models (Sun J et al., (1998) Oncogene 16: 1467-73.). Similarly, clinical trials on humans using a combination of anti-cancer drugs and the anti-HER2 monoclonal antibody, trastuzumab, with the aim of antagonizing the proto-oncogene receptor HER2/neu have achieved improved clinical response and overall survival of BRC patients (Molina M A, et al., (2001) Cancer Res.; 61(12): 4744-9.). Finally, a tyrosine kinase inhibitor, STI-571, which selectively inactivates bcr-abl fusion proteins, has been developed to treat chronic myelogenous leukemias, wherein constitutive activation of bcr-abl tyrosine kinase plays a crucial role in the transformation of leukocytes. Agents of these kind are designed to suppress the oncogenic activity of specific gene products (O'Dwyer M E & Druker B J. (2000) Curr Opin Oncol.; 12(6): 594-7). Accordingly, it is apparent that gene products commonly up-regulated in cancerous cells may serve as potential targets for developing novel anti-cancer agents.

It has been further demonstrated that CD8+ cytotoxic T lymphocytes (CTLs) recognize epitope peptides derived from tumor-associated antigens (TAAs) presented on the MHC Class I molecule, and lyse tumor cells. Since the discovery of the MAGE family as the first example of TAAs, many other TAAs have been discovered using immunological approaches (Boon, (1993) Int J Cancer 54: 177-80; Boon and van der Bruggen, (1996) J Exp Med 183: 725-9; van der Bruggen et al., (1991) Science 254: 1643-7; Brichard V et al., (1993) J Exp Med 178: 489-95; Kawakami Y et al., (1994) J Exp Med 180: 347-52.). Some of the newly discovered TAAs are currently undergoing clinical development as targets of immunotherapy. TAAs discovered so far include MAGE (van der Bruggen et al., (1991) Science 254: 1643-7.), gp100 (Kawakami Y et al., (1994) J Exp Med 180: 347-52.), SART (Shichijo S et al., (1998) J Exp Med 187: 277-88.), and NY-ESO-1 (Chen YT et al., (1997) Proc Natl Acad Sci USA 94: 1914-8.). On the other hand, gene products demonstrated to be specifically over-expressed in tumor cells have been shown to be recognized as targets inducing cellular immune responses. Such gene products include p 53 (Umano Y et al., (2001) Brit J Cancer 84: 1052-7.), HER2/neu (Tanaka H et al., (2001) Brit J Cancer 84: 94-9.), CEA (Nukaya I et al., (1999) Int J Cancer 80: 92-7.), and so on.

In spite of significant progress in basic and clinical research concerning TAAs (Rosenberg S A et al., (1998) Nature Med 4: 321-7.; Mukherji B et al., (1995) Proc Natl Acad Sci USA 92: 8078-82.; Hu X et al., (1996) Cancer Res 56: 2479-83.), only a limited number of candidate TAAs for the treatment of adenocarcinomas, including colorectal cancer, are currently available. TAAs abundantly expressed in cancer cells yet whose expression is restricted to cancer cells would be promising candidates as immunotherapeutic targets. Further, identification of new TAAs that induce potent and specific antitumor immune responses is expected to encourage the clinical use of peptide vaccination strategies for various types of cancer (Boon and van der Bruggen, (1996) J Exp Med 183: 725-9.; van der Bruggen et al., (1991) Science 254: 1643-7.; Brichard V et al., (1993) J Exp Med 178: 489-95.; Kawakami Y et al., (1994) J Exp Med 180: 347-52.; Shichijo S et al., (1998) J Exp Med 187: 277-88.; Chen Y T et al., (1997) Proc Natl Acad Sci USA 94: 1914-8.; Harris C C, (1996) J Natl Cancer Inst 88: 1442-5.; Butterfield L H et al., (1999) Cancer Res 59: 3134-42.; Vissers J L, et al., (1999) Cancer Res 59: 5554-9.; van der Burg S H et al., (1996) J Immunol 156: 3308-14.; Tanaka F et al., (1997) Cancer Res 57: 4465-8.; Fujie T et al., (1999) Int J Cancer 80: 169-72.; Kikuchi M et al., (1999) Int J Cancer 81: 459-66.; Oiso M et al., (1999) Int J Cancer 81: 387-94.).

It has been repeatedly reported that peptide-stimulated peripheral blood mononuclear cells (PBMCs) from certain healthy donors produce significant levels of IFN-α in response to the peptide, but rarely exert cytotoxicity against tumor cells in an HLA-A24 or A0201 restricted manner in $^{51}$Cr-release assays (Kawano K et al., (2000) Cancer Res 60: 3550-8.; Nishizaka S et al., (2000) Cancer Res 60: 4830-7.; Tamura M et al., (2001) Jpn J Cancer Res 92: 762-7.). However, both of HLA-A24 and HLA-A0201 are popular HLA alleles in the Japanese, as well as the Caucasian populations (Date Y et al., (1996) Tissue Antigens 47: 93-101.; Kondo A et al., (1995) J Immunol 155: 4307-12.; Kubo R T et al., (1994) J Immunol 152: 3913-24.; Imanishi T et al., (1992) Proceeding of the eleventh International Histocompatibility Workshop and Conference Oxford University Press, Oxford, 1065.; Williams F et al., (1997) Tissue Antigen 49: 129.). Thus, antigenic peptides of carcinomas presented by these HLAs may be especially useful for the treatment of carcinomas among the Japanese and Caucasian populations. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller M A et al., (1996) Proc Natl Acad Sci USA 93: 4102-7.).

SUMMARY OF THE INVENTION

The present invention is based on the discovery that the expression of the ZNFN3A1 gene is specifically and significantly elevated in breast cancer (BRC) cells. The nucleotide sequence and amino acid sequence of ZNFN3A1 (also referred to as "SMYD3") are set forth in SEQ ID NOs: 4 and 5, respectively. These sequences are also available from Genbank Accession NO. AB057595 under the gene symbol "SMYD3".

Accordingly, the present invention provides a method of diagnosing or determining a predisposition to BRC in a subject by determining an expression level of ZNFN3A1 in a patient-derived biological sample, such as tissue sample. A normal cell is one obtained from breast tissue. An alteration, e.g., an increase or decrease in the level of expression of a gene as compared to a normal control level of the gene, indicates that the subject suffers from or is at risk of developing BRC.

In the context of the present invention, the phrase "control level" refers to a protein expression level detected in a control sample and includes both a normal control level and a BRC control level. A control level can be a single expression profile derived from a single reference population or from a plurality of expression profiles. For example, the control level can be a database of expression profiles from previously tested cells. A "normal control level" refers to a level of gene expression detected in a normal, healthy individual or in a population of individuals known not to be suffering from BRC. A normal individual is one with no clinical symptoms of BRC. On the other hand, a "BRC control level" refers to an expression profile of ZNFN3A1 found in a population suffering from BRC.

An increase in the expression level of ZNFN3A1 detected in a test sample as compared to a normal control level indicates that the subject (from which the sample was obtained) suffers from or is at risk of developing BRC.

According to the present invention, a gene expression level is deemed "altered" when expression of the gene is increased or decreased by at least 10%, preferably at least 25%, more preferably at least 50% or more as compared to a control level. Alternatively, an expression level is deemed "increased" or "decreased" when gene expression is increased or decreased by at least 0.1, at least 0.2, at least 1, at least 2, at least 5, or at least 10 or more fold as compared to a control level. Expression can be determined by detecting hybridization, e.g., of a ZNFN3A1 probe to a gene transcript in the patient-derived tissue sample.

In the context of the present invention, the patient-derived tissue sample may be any tissue obtained from a test subject, e.g., a patient known to or suspected of having BRC. For example, the tissue may contain an epithelial cell. More particularly, the tissue may be an epithelial cell from a breast ductal carcinoma.

The present invention further provides methods of identifying an agent that inhibits or enhances the expression or activity of ZNFN3A1, by contacting a test cell expressing ZNFN3A1 with a test compound and determining the expression level of ZNFN3A1 or the activity of its gene product. The test cell may be an epithelial cell, such as an epithelial cell obtained from a breast carcinoma. A decrease in the expression level of ZNFN3A1 or the activity of its gene product as compared to the expression level or activity of its gene product detected in the absence of the test compound indicates that the test agent is an inhibitor of ZNFN3A1 and may therefore be used to reduce a symptom of BRC.

It is a further object of the present invention to provide a method for assessing or determining the prognosis of a patient with breast cancer by comparing a ZNFN3A1 level in a patient-derived biological sample with that of a control sample. An elevated expression level is indicative of poor survival. In particular, the higher the expression level of ZNFN3A1 measured in the patient derived sample, the poorer the prognosis for post-treatment remission, recovery and/or survival and the higher the likelihood of poor clinical outcome.

It is a further object of the present invention to provide a method for monitoring the course of treatment for breast cancer comprising the step of comparing the ZNFN3A1 level in a patient-derived biological sample taken subsequent to treatment with that of a patient-derived biological sample taken prior to treatment or with that of a control sample. A decrease in ZNFN3A1 expression level subsequent to treatment is indicative of efficacious treatment and/or positive prognosis. Conversely, an increase or lack of change in ZNFN3A1 expression level subsequent to treatment is indicative of inefficacious treatment and/or negative prognosis.

The present invention also provides a kit for detecting a breast cancer wherein the kit comprising a detection reagent which binds to ZNFN3A1 nucleic acids or polypeptides.

Therapeutic methods of the present invention include a method of treating or preventing BRC in a subject, including the step of administering to the subject an antisense composition. In the context of the present invention, the antisense composition reduces the expression of the specific target gene. For example, the antisense composition may contain a nucleotide which is complementary to the ZNFN3A1 sequence. Alternatively, the present method may include the step of administering to a subject a small interfering RNA (siRNA) composition. In the context of the present invention, the siRNA composition reduces the expression of ZNFN3A1. In yet another method, the treatment or prevention of BRC in a subject may be carried out by administering to a subject a ribozyme composition. In the context of the present invention, the nucleic acid-specific ribozyme composition reduces the expression of ZNFN3A1. In fact, the inhibitory effect of the siRNA for ZNFN3A1 is confirmed herein. For example, the working examples of the instant application clearly demonstrate that siRNA for ZNFN3A1 inhibit cell proliferation of BRC cells. Thus, in the present invention, ZNFN3A1 is preferred therapeutic target for breast cancer.

The present invention also includes vaccines and vaccination methods. For example, a method of treating or preventing BRC in a subject may involve administering to the subject a vaccine containing a polypeptide encoded by a nucleic acid of ZNFN3A1 or an immunologically active fragment of such a polypeptide. In the context of the present invention, an immunologically active fragment is a polypeptide that is shorter in length than the full-length, naturally-occurring protein yet which induces an immune response analogous to that induced by the full-length protein. For example, an immunologically active fragment should be at least 8 residues in length and capable of stimulating an immune cell, such as a T cell or a B cell. Immune cell stimulation can be measured by detecting cell proliferation, elaboration of cytokines (e.g., IL-2), and/or production of an antibody.

One advantage of the methods described herein is that the disease is identified prior to detection of overt clinical symptoms of BRC. Other objects, features and advantages of the present invention will be apparent when the following detailed description is read in conjunction with the accompanying figures and examples, as well as the claims appended hereto.

DETAILED DESCRIPTION OF THE INVENTION

Figure 1:
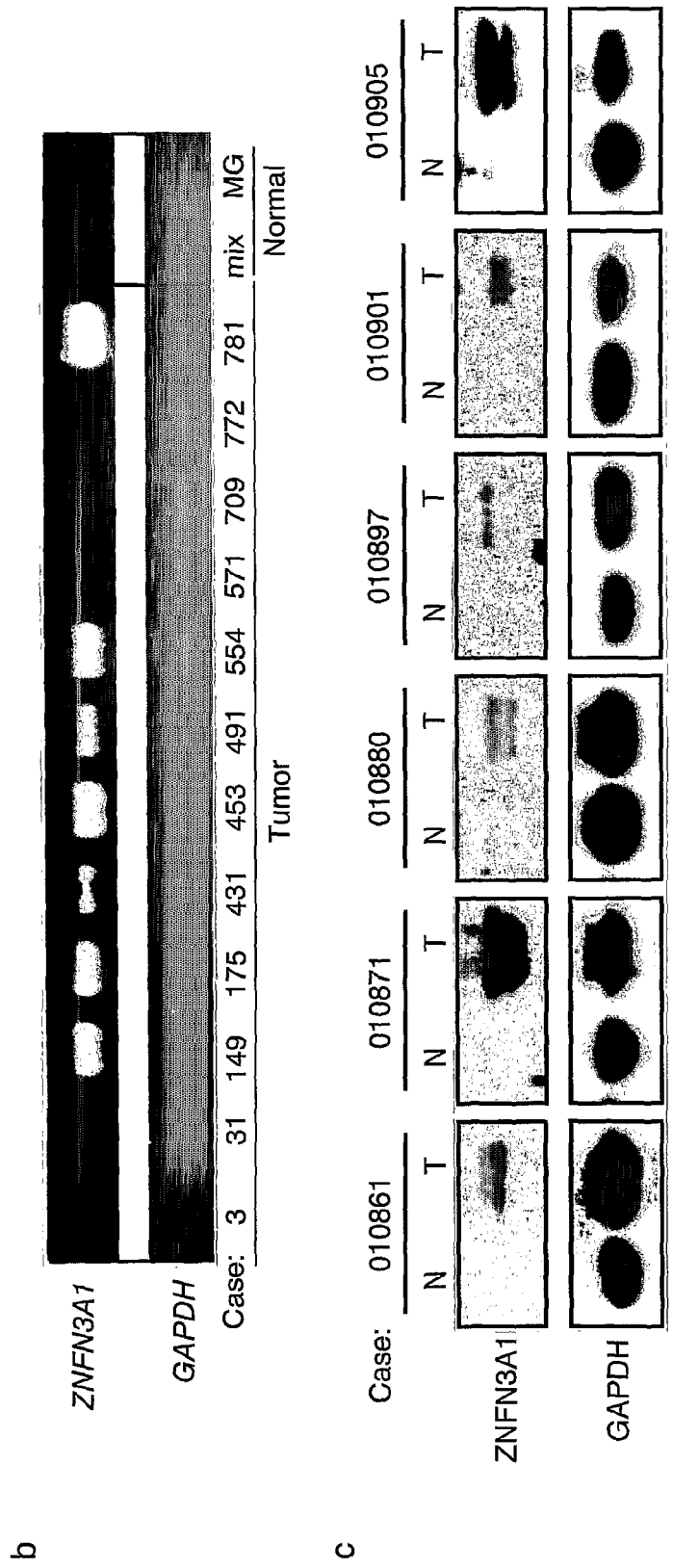
FIG. 1 depicts the elevated ZNFN3A1 expression associated with BRC tissues. Part (a) describes the number of samples showing elevated ZNFN3A1 expression with different criteria in the present microarray data of 92 BRC tissues with different histology. Part (b) depicts ZNFN3A1 expression in 12 cancer tissues, a mixture of normal ductal epithelial cells from 15 pre-menopausal patients (mix), and whole normal mammary gland (MG) analyzed by semi-quantitative RT-PCR. Expression of GAPDH served as an internal control. Part (c) depicts presence of the ZNFN3A1 protein in BRC tissues (T) and corresponding noncancerous mammary tissue (N), as measured by western blot analysis. Expression of GAPDH served as a control.

The words "a", "an" and "the" as used herein mean "at least one" unless otherwise specifically indicated.

All patents, patent applications, and publications cited herein are incorporated by reference in their entirety.

Unless otherwise defined, all technical and scientific terms used herein have the same meaning as commonly understood by one of ordinary skill in the art to which this invention belongs. However, in case of conflict, the present specification, including definitions, will control.

Generally, BRC cells exist as a solid mass having a highly inflammatory reaction and containing various cellular components. Therefore, previous published microarray data are likely to reflect heterogenous profiles.

The present invention is based in part of the discovery of elevated expression of ZNFN3A1 in cells from patients with BRC.

As shown in SEQ ID NO: 4, the ZNFN3A1 cDNA consists of 1622 nucleotides that contain an open reading frame of 1284 nucleotides encoding a putative 428-amino acid protein with a zinc finger motif. The zinc finger domain (MYND) is positioned at codons 49-87 and the SET (Su 3-9, Enhancer-of-zeste, Trihorrax) domain is positioned at codons 117-246. The ZNFN3A1 protein preferably includes the amino acid sequence set forth in SEQ. ID. NO.5.

The ZNFN3A1 gene has been previously identified as a gene whose expression is up-regulated in hepatocellular carcinoma and colorectal cancer (see WO 2003/027143). In addition, siRNA of ZNFN3A1 have demonstrated utility in the treatment of hepatocellular carcinoma and colorectal adenocarcinoma (see WO 2004/76623). Interestingly, subcellular localization of ZNFN3A1 protein has been shown to be altered during cell cycle progression or due to the density of cultured cells; it specifically accumulates in the nucleus when cells are in middle to late S phase or cultured in sparse condition, while it localizes in the cytoplasm as well as nucleus when they are in other phases or grown in dense condition. Furthermore, ZNFN3A1 has been shown to directly associate with a RNA helicase KIAA0054, and form a complex with RNA polymerase II, which then activates transcription of downstream genes including epidermal growth factor receptor (EGFR) through a direct binding of the complex with an element of "(C)CCCTCC(T)" in the 5' flanking region. Exogenous expression of ZNFN3A1 into NIH3T3 cells has been shown to confer increased cell growth, while suppression of its expression with antisense S-oligonucleotides has resulted in a significant growth-inhibition of cancer cells. These findings suggest that ZNFN3A1 renders oncogenic activities to cancer cells by transcriptional activation of target genes including EGFR through a complex with RNA helicase and RNA polymerase II. Given that its expression is elevated in cells obtained from patients with BRC, inhibition of the activity of ZNFN3A1 or its complex represent a promising strategy for the treatment of BRC.

Herein, the analysis of ninety-two (92) breast carcinomas using cDNA-microarray revealed that ZNFN3A1 expression was elevated in 36 of 69 invasive ductal carcinomas (IDC) and in 6 of 11 ductal carcinoma in situ (DCIS), when the cut-off of tumor to normal tissue ratio was greater than two. Accordingly, the present invention relates to the diagnostic utility of ZNFN3A1 identified as a marker of BRC and as a BRC gene target, the expression of which may be altered to treat or alleviate a symptom of BRC. In particular, by measuring the expression of ZNFN3A1 in a sample of cells, BRC can be diagnosed. Similarly, measuring the expression of ZNFN3A1 in response to various agents can identify agents for treating BRC.

The present invention involves determining (e.g., measuring) the expression of ZNFN3A1. Using sequence information provided by the GenBank™ database entries for known sequences, the ZNFN3A1 can be detected and measured using techniques well known to those of ordinary skill in the art. For example, sequences within the sequence database entries corresponding to ZNFN3A1, can be used to construct probes for detecting RNA sequences corresponding to ZNFN3A1 in, e.g., Northern blot hybridization analyses. As another example, the sequences can be used to construct primers for specifically amplifying the ZNFN3A1 nucleic acid in, e.g., amplification-based detection methods, such as reverse-transcription based polymerase chain reaction.

Expression level of ZNFN3A1 in a test cell population, e.g., a patient-derived tissues sample, is then compared to the expression level of ZNFN3A1 in a reference population. The reference cell population includes one or more cells for which the compared parameter is known, i.e., breast ductal carcinoma cells (e.g., BRC cells) or normal breast ductal epithelial cells (e.g., non-BRC cells).

Whether or not a pattern of gene expression in a test cell population as compared to a reference cell population indicates BRC or a predisposition thereto depends upon the composition of the reference cell population. For example, if the reference cell population is composed of non-BRC cells, a similarity in gene expression profile between the test cell population and the reference cell population indicates the test cell population is non-BRC. Conversely, if the reference cell population is made up of BRC cells, a similarity in gene expression profile between the test cell population and the reference cell population indicates that the test cell population includes BRC cells.

A level of expression of ZNFN3A1 gene in a test cell population is considered "altered" if it varies from the expression level of the corresponding ZNFN3A1 gene in a reference cell population by more than 1.1, more than 1.5, more than 2.0, more than 5.0, more than 10.0 or more fold.

Differential gene expression between a test cell population and a reference cell population can be normalized to a control nucleic acid, e.g. a housekeeping gene. For example, a control nucleic acid is one which is known not to differ depending on the cancerous or non-cancerous state of the cell. The expression level of a control nucleic acid can be used to normalize signal levels in the test and reference populations. Exemplary control genes include, but are not limited to, e.g., β-actin, glyceraldehyde 3-phosphate dehydrogenase and ribosomal protein P1.

The test cell population can be compared to multiple reference cell populations. Each of the multiple reference populations may differ in the known parameter. Thus, a test cell population may be compared to a first reference cell population known to contain, e.g., BRC cells, as well as a second reference population known to contain, e.g., non-BRC cells (normal cells). The test cell may be included in a tissue type or cell sample from a subject known to contain, or suspected of containing, BRC cells.

The test cell is preferably obtained from a bodily tissue or a bodily fluid, e.g., biological fluid (such as blood, urine or sputum, for example). For example, the test cell may be purified from breast tissue. Preferably, the test cell population comprises an epithelial cell. The epithelial cell is preferably from a tissue known to be or suspected to be a breast ductal carcinoma.

Cells in the reference cell population should be derived from a tissue type similar to that of the test cell. Optionally, the reference cell population is a cell line, e.g. a BRC cell line (i.e., a positive control) or a normal non-BRC cell line (i.e., a negative control). Alternatively, the control cell population may be derived from a database of molecular information derived from cells for which the assayed parameter or condition is known.

The subject is preferably a mammal. Exemplary mammals include, but are not limited to, e.g., a human, non-human primate, mouse, rat, dog, cat, horse, or cow.

Expression of ZNFN3A1 disclosed herein can be determined at the protein or nucleic acid level, using methods known in the art. For example, Northern hybridization analysis, using probes which specifically recognize the sequence, can be used to determine gene expression. Alternatively, gene expression may be measured using reverse-transcription-based PCR assays, e.g., using primers specific for the ZNFN3A1 sequence. Expression may also be determined at the protein level, i.e., by measuring the level of a polypeptide encoded by a gene described herein, or the biological activity thereof. Such methods are well known in the art and include, but are not limited to, e.g., immunoassays that utilize antibodies to protein encoded by the gene. The biological activities of the protein encoded by the ZNFN3A1 gene are generally well known in the art. For example, ZNFN3A1 has been shown to interact with HELZ (RNA helicase) or RNA polymerase II and to have methyl transferase activity (see WO 2005/71102, the entire contents of which are hereby incorporated by reference herein).

Diagnosing BRC:

In the context of the present invention, BRC is diagnosed by measuring the expression level of ZNFN3A1 in a test population of cells, (i.e., a patient-derived biological sample). Preferably, the test cell population contains an epithelial cell, e.g., a cell obtained from breast tissue. Gene expression can also be measured from blood or other bodily fluids, such as urine. Other biological samples can be used for measuring protein levels. For example, the protein level in blood or serum derived from a subject to be diagnosed can be measured by immunoassay or other conventional biological assay.

According to the present invention, expression of ZNFN3A1 is determined in the test cell or biological sample and compared to the normal control expression level associated with ZNFN3A1. A normal control level is an expression profile of ZNFN3A1 typically found in a population known not to be suffering from BRC. An alteration (e.g., an increase) in the level of expression in the patient-derived tissue sample of ZNFN3A1 indicates that the subject is suffering from or is at risk of developing BRC. For example, an increase in the expression of ZNFN3A1 in the test population as compared to the normal control level indicates that the subject is suffering from or is at risk of developing BRC.

Alteration of ZNFN3A1 in the test population as compared to the normal control level indicates that the subject suffers from or is at risk of developing BRC.

Identifying Agents that Inhibit ZNFN3A1 Expression:

An agent that inhibits the expression of ZNFN3A1, or the activity of its gene product, can be identified by contacting a test cell population expressing ZNFN3A1 with a test agent and then determining the expression level of ZNFN3A1 or the activity of its gene product. A decrease in the level of expression of ZNFN3A1 or in the level of activity of its gene product in the presence of the agent as compared to the expression or activity level in the absence of the test agent indicates that the agent is an inhibitor of ZNFN3A1 and useful in inhibiting BRC.

The test cell population may be any cell expressing ZNFN3A1. For example, the test cell population may contain an epithelial cell, such as a cell derived from breast tissue. Furthermore, the test cell may be an immortalized cell line derived from an carcinoma cell. Alternatively, the test cell may be a cell which has been transfected with ZNFN3A1 or which has been transfected with a regulatory sequence (e.g. promoter sequence) from ZNFN3A1 operably linked to a reporter gene.

Assessing Efficacy of Treatment of BRC in a Subject:

The differentially expressed ZNFN3A1 identified herein also allow for the course of treatment of BRC to be monitored. In this method, a test cell population is provided from a subject undergoing treatment for BRC. If desired, test cell populations are obtained from the subject at various time points, before, during, and/or after treatment. Expression of ZNFN3A1 in the cell population is then determined and compared to a reference cell population, which includes cells whose BRC state is known. In the context of the present invention, the reference cells should not have been exposed to the treatment of interest.

If the reference cell population contains no BRC cells, a similarity in the expression of ZNFN3A1 in the test cell population and the reference cell population indicates that the treatment of interest is efficacious. However, a difference in the expression of ZNFN3A1 in the test population and a normal control reference cell population indicates a less favorable clinical outcome or prognosis. Similarly, if the reference cell population contains BRC cells, a difference between the expression of ZNFN3A1 in the test cell population and the reference cell population indicates that the treatment of interest is efficacious, while a similarity in the expression of ZNFN3A1 in the test population and a cancer control reference cell population indicates a less favorable clinical outcome or prognosis.

Additionally, the expression level of ZNFN3A1 determined in a subject-derived biological sample obtained after treatment (i.e., post-treatment levels) can be compared to the expression level of ZNFN3A1 determined in a subject-derived biological sample obtained prior to treatment onset (i.e., pre-treatment levels). A decrease in the expression level of ZNFN3A1. in a post-treatment sample indicates that the treatment of interest is efficacious while an increase or maintenance in the expression level in the post-treatment sample indicates a less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of breast ductal carcinoma in a subject. When a treatment of interest is applied prophylactically, the term "efficacious" means that the treatment retards or prevents a breast tumor from forming or retards, prevents, or alleviates a symptom of clinical BRC. Assessment of breast tumors can be made using standard clinical protocols.

In addition, efficaciousness can be determined in association with any known method for diagnosing or treating BRC. BRC can be diagnosed, for example, by identifying symptomatic anomalies, e.g., weight loss, abdominal pain, back pain, anorexia, nausea, vomiting and generalized malaise, weakness, and jaundice.

Selecting a Therapeutic Agent for Treating BRC That is Appropriate for a Particular Individual:

Differences in the genetic makeup of individuals can result in differences in their relative abilities to metabolize various drugs. An agent that is metabolized in a subject to act as an anti-BRC agent can manifest itself by inducing a change in a gene expression pattern in the subject's cells from that characteristic of a cancerous state to a gene expression pattern characteristic of a non-cancerous state. Accordingly, the differentially expressed ZNFN3A1 disclosed herein allow for a putative therapeutic or prophylactic inhibitor of BRC to be tested in a test cell population from a selected subject in order to determine if the agent is a suitable inhibitor of BRC in the subject.

To identify an inhibitor of BRC that is appropriate for a specific subject, a test cell population from the subject is exposed to a therapeutic agent, and the expression of ZNFN3A1 is determined.

In the context of the method of the present invention, the test cell population contains a BRC cell expressing ZNFN3A1. Preferably, the test cell is an epithelial cell. For example, a test cell population may be incubated in the presence of a candidate agent and the pattern of gene expression of the test cell population may be measured and compared to one or more reference profiles, e.g., a BRC reference expression profile or a non-BRC reference expression profile that includes ZNFN3A1.

A decrease in the expression of ZNFN3A1 in a test cell population relative to a reference cell population containing BRC indicates that the agent has therapeutic potential.

In the context of the present invention, the test agent can be any compound or composition. Exemplary test agents include, but are not limited to, immunomodulatory agents.

Screening Assays for Identifying Therapeutic Agents:

The differentially expressed ZNFN3A1 disclosed herein can also be used to identify candidate therapeutic agents for treating BRC. The method of the present invention involves screening a candidate therapeutic agent to determine if it can convert an expression profile of ZNFN3A1 characteristic of a BRC state to a gene expression profile characteristic of a non-BRC state.

In the instant method, a cell is exposed to a test agent or a plurality of test agents (sequentially or in combination) and the expression of ZNFN3A1 in the cell is measured. The expression profile of ZNFN3A1 assayed in the test population is compared to an expression level of ZNFN3A1 detected in a reference cell population that is not exposed to the test agent.

An agent capable of suppressing the expression of an overexpressed gene, such as ZNFN3A1, has potential clinical benefit. Such agents may be further tested for the ability to prevent breast ductal carcinomal growth in animals or test subjects.

In a further embodiment, the present invention provides methods for screening candidate agents which act on the potential targets in the treatment of BRC. As discussed in detail above, by controlling the expression levels of ZNFN3A1 or the activity of its gene products, one can control the onset and progression of BRC. Thus, candidate agents, which act on the potential targets in the treatment of BRC, can be identified through screening methods that use such expression levels and activities as indices of the cancerous or non-cancerous state. In the context of the present invention, such screening may comprise, for example, the following steps:
  a) contacting a test compound with a polypeptide encoded by a polynucleotide of ZNFN3A1;
  b) detecting the binding activity between the polypeptide and the test compound; and
  c) selecting the test compound that binds to the polypeptide.

Alternatively, the screening method of the present invention may comprise the following steps:
  a) contacting a candidate compound with a cell expressing ZNFN3A1; and
  b) selecting the candidate compound that reduces the expression level of ZNFN3A1 as compared to the expression level of ZNFN3A1 detected in the absence of the candidate compound.

Cells expressing ZNFN3A1 gene include, for example, cell lines established from BRC; such cells can be used for the above screening of the present invention.

Alternatively, the screening method of the present invention may comprise the following steps:
  a) contacting a test compound with a polypeptide encoded by a polynucleotide of ZNFN3A1;
  b) detecting the biological activity of the polypeptide of step (a); and
  c) selecting a compound that suppresses the biological activity of the polypeptide encoded by the polynucleotide of ZNFN3A1 as compared to the biological activity detected in the absence of the test compound.

A protein for use in the screening method of the present invention can be obtained as a recombinant protein using the nucleotide sequence of ZNFN3A1. Based on the information regarding ZNFN3A1 and its encoded protein, one skilled in the art can select any biological activity of the protein as an index for screening and any suitable measurement method to assay for the selected biological activity.

Alternatively, the screening method of the present invention may comprise the following steps:
  a) contacting a candidate compound with a cell into which a vector, comprising the transcriptional regulatory region of ZNFN3A1 and a reporter gene that is expressed under the control of the transcriptional regulatory region, has been introduced;
  b) measuring the expression level or activity of said reporter gene; and
  c) selecting the candidate compound that reduces the expression level or activity of said reporter gene as compared to the expression level or activity of said reporter gene detected in the absence of the candidate compound.

Suitable reporter genes and host cells are well known in the art. A reporter construct suitable for the screening method of the present invention can be prepared by using the transcriptional regulatory region of ZNFN3A1. When the transcriptional regulatory region of ZNFN3A1 is known to those skilled in the art, a reporter construct can be prepared by using the previous sequence information. When the transcriptional regulatory region of ZNFN3A1 remains unidentified, a nucleotide segment containing the transcriptional regulatory region can be isolated from a genome library based on the nucleotide sequence information of ZNFN3A1.

A compound isolated by the screening serves as a candidate for the development of drugs that inhibit the expression of ZNFN3A1 or the activity of the protein encoded by ZNFN3A1 and can be applied to the treatment or prevention of BRC.

Moreover, compounds in which a part of the structure of the compound inhibiting the activity of protein encoded by ZNFN3A1 is converted by addition, deletion and/or replacement are also included as the compounds obtainable by the screening method of the present invention.

When administrating a compound isolated by the method of the present invention as a pharmaceutical for humans and other mammals, including, but not limited to, mice, rats, guinea-pigs, rabbits, cats, dogs, sheep, pigs, cattle, monkeys, baboons, and chimpanzees, the isolated compound can be directly administered or can be formulated into a dosage form using known pharmaceutical preparation methods. Pharmaceutical compositions and preparations contemplated by the present invention, as well as methods of making and using same, are further described in a subsequent section. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmaceutically acceptable carriers or media, including, but not limited to, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredient contained in such a preparation makes a suitable dosage within the indicated range acquirable.

Examples of additives that can be admixed into tablets and capsules include, but are not limited to, binders, such as gelatin, corn starch, tragacanth gum and arabic gum; excipients, such as crystalline cellulose; swelling agents, such as corn starch, gelatin and alginic acid; lubricants, such as magnesium stearate; sweeteners, such as sucrose, lactose or saccharin; and flavoring agents, such as peppermint, Gaultheria adenothrix oil and cherry. When the unit-dose form is a capsule, a liquid carrier, such as an oil, can be further included in the above ingredients. Sterile composites for injection can be formulated following normal drug implementations using vehicles, such as distilled water, suitable for injection.

Physiological saline, glucose, and other isotonic liquids, including adjuvants, such as D-sorbitol, D-mannose, D-mannitol, and sodium chloride, can be used as aqueous solutions for injection. These can be used in conjunction with suitable solubilizers, such as alcohol, for example, ethanol; polyalcohols, such as propylene glycol and polyethylene glycol; and non-ionic surfactants, such as Polysorbate 80 (TM) and HCO-50.

Sesame oil or soy-bean oil are examples of oleaginous liquids that may be used in conjunction with benzyl benzoate or benzyl alcohol as a solubilizer, and may be formulated with a buffer, such as phosphate buffer and sodium acetate buffer; a pain-killer, such as procaine hydrochloride; a stabilizer, such as benzyl alcohol and phenol; and/or an anti-oxidant. A prepared injection may be filled into a suitable ampoule.

Methods well known to those skilled in the art may be used to administer the pharmaceutical composition of the present invention to patients, for example as an intraarterial, intravenous, or percutaneous injection or as an intranasal, transbronchial, intramuscular or oral administration. The dosage and method of administration vary according to the body-weight and age of a patient and the administration method; however, one skilled in the art can routinely select a suitable method of administration. If said compound is encodable by a DNA, the DNA can be inserted into a vector for gene therapy and the vector administered to a patient to perform the therapy. The dosage and method of administration vary according to the body-weight, age, and symptoms of the patient; however, the selection and optimization of these parameters is within the purview of one skilled in the art.

For example, although the dose of a compound that binds to a protein of the present invention and regulates its activity depends on the symptoms, the dose is generally about 0.1 mg to about 100 mg per day, preferably about 1.0 mg to about 50 mg per day and more preferably about 1.0 mg to about 20 mg per day, when administered orally to a normal adult human (weight 60 kg).

When administering the compound parenterally, in the form of an injection to a normal adult human (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount may be routinely calculated by converting to 60 kgs of body-weight.

Assessing the Prognosis of a Subject with BRC:

The present invention also provides a method of assessing the prognosis of a subject with BRC including the step of comparing the expression of ZNFN3A1 in a test cell population to the expression of ZNFN3A1 in a reference cell population derived from patients over a spectrum of disease stages. By comparing the gene expression of ZNFN3A1 in the test cell population and the reference cell population(s), or by comparing the pattern of gene expression over time in test cell populations derived from the subject, the prognosis of the subject can be assessed.

For example, an increase in the expression of ZNFN3A1 as compared to a normal control indicates less favorable prognosis. Conversely, a similarity in the expression of ZNFN3A1 as compared to normal control indicates a more favorable prognosis for the subject. Preferably, the prognosis of a subject can be assessed by comparing the expression profile of ZNFN3A1.

Kits:

The present invention also provides a kit for detecting a breast cancer, the kit includes a BRC-detection reagent, e.g., a nucleic acid that specifically binds to or identifies ZNFN3A1 nucleic acids, such as oligonucleotide sequences which are complementary to a portion of ZNFN3A1 nucleic acid, or an antibody that bind to proteins encoded by ZNFN3A1 nucleic acid. The detection reagents may be packaged together in the form of a kit. For example, the detection reagents may be packaged in separate containers, e.g. a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay may also be included in the kit. The assay format of the kit may be a Northern hybridization or a sandwich ELISA, both of which are known in the art.

For example, a BRC detection reagent may be immobilized on a solid matrix, such as a porous strip, to form at least one BRC detection site. The measurement or detection region of the porous strip may include a plurality of sites, each containing a nucleic acid. A test strip may also contain sites for negative and/or positive controls. Alternatively, control sites may be located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of BRC present in the sample. The detection sites may be configured in any suitably detectable shape and are typically in the shape of a bar or dot spanning the width of a test strip.

Methods of Inhibiting BRC:

The present invention further provides a method for treating or alleviating a symptom of BRC in a subject by decreasing the expression of ZNFN3A1 (or the activity of its gene product). Suitable therapeutic compounds can be administered prophylactically or therapeutically to a subject suffering from or at risk of (or susceptible to) developing BRC. Such subjects can be identified using standard clinical methods or by detecting an aberrant level of expression of ZNFN3A1 or aberrant activity of its gene product. In the context of the present invention, suitable therapeutic agents include, for example, inhibitors of cell cycle regulation and cell proliferation.

Alternatively, the therapeutic method of the present invention may include the step of decreasing the expression, function, or both, of gene products of ZNFN3A1 whose expression is aberrantly increased ("up-regulated" or "over-expressed" gene) in breast cells. Expression may be inhibited in any of several ways known in the art. For example, expression can be inhibited by administering to the subject a nucleic acid that inhibits, or antagonizes the expression of the over-expressed gene, e.g., an antisense oligonucleotide or small interfering RNA which disrupts expression of the over-expressed gene.

Antisense Nucleic Acids and siRNA:

As noted above, antisense nucleic acids corresponding to the nucleotide sequence of ZNFN3A1 can be used to reduce the expression level of the gene. Antisense nucleic acids corresponding to ZNFN3A1 that are up-regulated in BRC are useful for the treatment of BRC. Specifically, the antisense nucleic acids of the present invention may act by binding to nucleotide sequence of ZNFN3A1, or mRNAs corresponding thereto, thereby inhibiting the transcription or translation of the genes, promoting the degradation of the mRNAs, and/or inhibiting the expression of proteins encoded by ZNFN3A1, thereby, inhibiting the function of the protein. The term "antisense nucleic acids" as used herein encompasses both nucleotides that are entirely complementary to the target sequence and those having a mismatch of one or more nucleotides, so long as the antisense nucleic acids can specifically hybridize to the target sequences. For example, the antisense nucleic acids of the present invention include polynucleotides that have a homology of at least 70% or higher, preferably at least 80% or higher, more preferably at least 90% or higher, even more preferably at least 95% or higher over a span of at least 15 continuous nucleotides. Algorithms known in the art can be used to determine the homology.

The antisense nucleic acid of the present invention act on cells producing the proteins encoded by ZNFN3A1 by binding to the DNA or mRNA encoding the protein, inhibiting their transcription or translation, promoting the degradation of the mRNA, and inhibiting the expression of the protein, thereby resulting in the inhibition of the protein function.

An antisense nucleic acid of the present invention can be made into an external preparation, such as a liniment or a poultice, by admixing it with a suitable base material which is inactive against the nucleic acid.

Also, as needed, the antisense nucleic acids of the present invention can be pharmaceutically formulated, for example, into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following known methods.

The antisense nucleic acids of the present invention can be given to the patient by direct application onto the ailing site or by injection into a blood vessel so that it will reach the site of ailment. An antisense-mounting medium can also be used to increase durability and membrane-permeability. Examples include, but are not limited to, liposomes, poly-L-lysine, lipids, cholesterol, lipofectine or derivatives of these.

The dosage of the antisense nucleic acid derivative of the present invention can be adjusted suitably according to the patient's condition and used in desired amounts. For example, a dose range of 0.1 to 100 mg/kg, preferably 0.1 to 50 mg/kg can be administered.

The antisense nucleic acids of the present invention inhibit the expression of a protein of the present invention and are thereby useful for suppressing the biological activity of the protein of the invention. In addition, expression-inhibitors, comprising antisense nucleic acids of the present invention, are useful in that they can inhibit the biological activity of a protein of the present invention.

The method of the present invention can be used to alter the expression in a cell of ZNFN3A1, e.g., up-regulation resulting from the malignant transformation of the cells. Binding of the siRNA to a transcript corresponding to ZNFN3A1 in the target cell results in a reduction in the protein production by the cell.

The antisense nucleic acids of present invention include modified oligonucleotides. For example, thioated oligonucleotides may be used to confer nuclease resistance to an oligonucleotide.

Also, an siRNA against ZNFN3A1 can be used to reduce the expression level of ZNFN3A1. Herein, term "siRNA" refers to a double stranded RNA molecule which prevents translation of a target mRNA. Standard techniques for introducing siRNA into the cell may be used, including those in which DNA is a template from which RNA is transcribed. In the context of the present invention, the siRNA comprises a sense nucleic acid sequence and an anti-sense nucleic acid sequence against an up-regulated marker gene, such as ZNFN3A1. The siRNA is constructed such that a single transcript has both the sense and complementary antisense sequences of the target gene, e.g., a hairpin.

An siRNA of ZNFN3A1 hybridizes to target mRNA and thereby decreases or inhibits production of the polypeptides encoded by ZNFN3A1 by associating with the normally single-stranded mRNA transcript, thereby interfering with translation and thus, expression of the protein. Thus, siRNA molecules of the invention can be defined by their ability to hybridize specifically to mRNA of ZNFN3A1 under stringent conditions. For the purposes of this invention the terms "hybridize" or "hybridize specifically" are used to refer the ability of two nucleic acid molecules to hybridize under "stringent hybridization conditions." The phrase "stringent hybridization conditions" as used herein refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times of background, preferably 10 times of background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 50° C.

In the context of the present invention, an siRNA is preferably 500, 200, 100, 50, or 25 nucleotides or less in length. More preferably, an siRNA oligonucleotide is about 19-25 nucleotides in length. Exemplary nucleic acid sequence for the production of ZNFN3A1 siRNA includes the sequences of nucleotides of SEQ ID NO: 1 as the target sequence. In order to enhance the inhibition activity of the siRNA, nucleotide "u", can be added to 3'end of the antisense strand of the target sequence. The number of "u"s to be added is at least 2, generally 2 to 10, preferably 2 to 5. The added "u"s form single strand at the 3'end of the antisense strand of the siRNA.

An siRNA of ZNFN3A1 can be directly introduced into the cells in a form that is capable of binding to the mRNA transcripts. In these embodiments, the siRNA molecules of the invention are typically modified as described above for antisense molecules. Other modifications are also possible, for example, cholesterol-conjugated siRNAs have shown improved pharmacological properties (Song et al., (2003) *Nature Med.* 9: 347-51.). Alternatively, a DNA encoding the siRNA may be carried in a vector.

Vectors may be produced, for example, by cloning ZNFN3A1 target sequence into an expression vector having operatively-linked regulatory sequences flanking the sequence in a manner that allows for expression (by transcription of the DNA molecule) of both strands (Lee, N. S. et al., (2002) Nature Biotechnology 20: 500-5.). An RNA molecule that is antisense to mRNA of ZNFN3A1 is transcribed by a first promoter (e.g., a promoter sequence 3' of the cloned DNA) and an RNA molecule that is the sense strand for the mRNA of ZNFN3A1 is transcribed by a second promoter (e.g., a promoter sequence 5' of the cloned DNA). The sense and antisense strands hybridize in vivo to generate siRNA constructs for silencing of ZNFN3A1. Alternatively, the two constructs can be utilized to create the sense and anti-sense strands of a siRNA construct. Cloned ZNFN3A1 can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence that specifically hybridizes to an mRNA or a cDNA of ZNFN3A1. In preferred embodiments, [A] is a ribonucleotide sequence corresponding a sequence of ZNFN3A1,

[B] is a ribonucleotide sequence consisting of 3 to 23 nucleotides, and

[A'] is a ribonucleotide sequence consisting of the complementary sequence of [A]. The region [A] hybridizes to [A'], and then a loop consisting of region [B] is formed. The loop sequence may be preferably 3 to 23 nucleotide in length. The loop sequence, for example, can be selected from group consisting of following sequences (world-wide web.ambion.com/techlib/tb/tb_506.html). Furthermore, loop sequence consisting of 23 nucleotides also provides active siRNA (Jacque, J.-M. et al, (2002) Nature 418: 435-8.).

CCC, CCACC or CCACACC: Jacque, J. M, et al., (2002) Nature, Vol. 418: 435-8.

UUCG: Lee, N. S., et al., (2002) Nature Biotechnology 20: 500-5. Fruscoloni, P., et al., (2003) Proc. Natl. Acad. Sci. USA 100(4): 1639-44.

UUCAAGAGA: Dykxhoorn, D. M., et al., (2002) Nature Reviews Molecular Cell Biology 4: 457-67.

Accordingly, the loop sequence can be selected from group consisting of, CCC, UUCG, CCACC, CCACACC, and UUCAAGAGA. Preferable loop sequence is UUCAAGAGA ("ttcaagaga" in DNA). Exemplary hairpin siRNA suitable for use in the context of the present invention include:
for ZNFN3A1-siRNA (for target sequence of SEQ ID NO: 1)
5'-aacaucuaccagcugaaggug-[b]-caccuucagcugguagauguu-3' (SEQ ID NO: 2) and
5'-aacaucuaccagcugaaggug-[b]-caccuucagcugguagauguu-3' (SEQ ID NO: 3)

The nucleotide sequence of suitable siRNAs can be designed using an siRNA design computer program available from the Ambion website (world-wide web.ambion.com/techlib/misc/siRNA_fmder.html). The computer program selects nucleotide sequences for siRNA synthesis based on the following protocol.
Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. don't recommend against designing siRNA to the 5' and 3' untranslated regions (JTRs) and regions near the start codon (within 75 bases) as these may be richer in regulatory protein binding sites. UTR-binding proteins and/or translation initiation complexes may interfere with binding of the siRNA endonuclease complex.
2. Compare the potential target sites to the human genome database and eliminate from consideration any target sequences with significant homology to other coding sequences. The homology search can be performed using BLAST, which can be found on the NCBI server at: world-wide web.ncbi.nlm.nih.gov/BLAST/.
3. Select qualifying target sequences for synthesis. At Ambion, preferably several target sequences can be selected along the length of the gene to evaluate.

The regulatory sequences flanking ZNFN3A1 gene sequences can be identical or different, such that their expression can be modulated independently, or in a temporal or spatial manner. siRNAs are transcribed intracellularly by cloning ZNFN3A1 templates, respectively, into a vector containing, e.g., a RNA polymerase III transcription unit from the small nuclear RNA (snRNA) U6 or the human H1 RNA promoter. For introducing the vector into the cell, transfection-enhancing agent can be used. FuGENE (Roche diagnostices), Lipofectamine 2000 (Invitrogen), Oligofectamine (Invitrogen), and Nucleofector (Wako pure Chemical) are useful as the transfection-enhancing agent.

The antisense oligonucleotide or siRNA of the present invention inhibits the expression of a polypeptide of the present invention and is thereby useful for suppressing the biological activity of a polypeptide of the invention. Also, expression-inhibitors, comprising the antisense oligonucleotide or siRNA of the invention, are useful in the point that they can inhibit the biological activity of the polypeptide of the invention. Therefore, a composition comprising an antisense oligonucleotide or siRNA of the present invention is useful for treating a BRC.

Furthermore, the present invention provides ribozymes that inhibit the expression of the ZNFN3A1 polypeptide of the present invention. Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi M et al., (1988) FEBS Lett 228: 228) and hairpin type ribozymes (Buzayan, (1986) Nature 323: 349; Kikuchi Y and Sasaki N, (1991) Nucleic Acids Res 19: 6751) are included in the small ribozymes. Methods for designing and constructing ribozymes are known in the art (see Koizumi M et al., (1988) FEBS Lett 228: 228; Koizumi M et al., (1989) Nucleic Acids Res 17: 7059; Kikuchi Y and Sasaki N, (1991) Nucleic Acids Res 19: 6751). Thus, ribozymes inhibiting the expression of the polypeptides of the present invention can also be constructed based on their sequence information (SEQ ID NO: 4) and these conventional methods.

Ribozymes against the ZNFN3A1 transcript inhibit the expression of the over-expressed ZNFN3A1 protein and can suppress the biological activity of the protein. Therefore, the ribozymes are useful in treating or preventing breast cancer.
Antibodies:

Alternatively, the activity or function of a gene product of ZNFN3A1, which is over-expressed in BRC, can be inhibited by administering a compound that binds to or otherwise inhibits the function of the gene products. For example, the compound is an antibody which binds to the gene product of ZNFN3A1.

The present invention refers to the use of antibodies, particularly antibodies against a protein encoded by ZNFN3A1, or a fragment of such an antibody. As used herein, the term "antibody" refers to an immunoglobulin molecule having a specific structure, that interacts (i.e., binds) only with the antigen that was used for synthesizing the antibody (i.e., the gene product of an up-regulated marker) or with an antigen closely related thereto. Furthermore, an antibody may be a fragment of an antibody or a modified antibody, so long as it binds to the protein encoded by ZNFN3A1. For instance, the antibody fragment may be Fab, F(ab')$_2$, Fv, or single chain Fv (scFv), in which Fv fragments from H and L chains are ligated by an appropriate linker (Huston J. S. et al., (1988) Proc. Natl. Acad. Sci. U.S.A. 85: 5879-83.). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al., (1994) J. Immunol. 152: 2968-76.; Better M. and Horwitz A. H. (1989) Methods Enzymol. 178: 476-96.; Pluckthun A. and Skerra A. (1989) Methods Enzymol. 178: 497-515.; Lamoyi E. (1986) Methods Enzymol. 121: 652-63.; Rousseaux J. et al., (1986) Methods Enzymol. 121: 663-9.; Bird R. E. and Walker B. (1991) W. Trends Biotechnol. 9: 132-7.).

An antibody may be modified by conjugation with a variety of molecules, such as, for example, polyethylene glycol (PEG). The present invention provides such modified antibodies. The modified antibody can be obtained by chemically modifying an antibody. Such modification methods are conventional in the field.

Alternatively, an antibody may comprise a chimeric antibody having a variable region derived from a nonhuman antibody and a constant region derived from a human antibody, or a humanized antibody, comprising a complementarity determining region (CDR) derived from a nonhuman antibody, a frame work region (FR) and a constant region derived from a human antibody. Such antibodies can be prepared by using known technologies. Humanization can be performed by substituting rodent CDRs or CDR sequences for the corresponding sequences of a human antibody (see e.g., Verhoeyen M et al., (1988) Science 239: 1534-6.). Accordingly, such humanized antibodies are chimeric antibodies, wherein substantially less than an intact human variable domain has been substituted by the corresponding sequence from a non-human species.

Fully human antibodies, comprising human variable regions in addition to human framework and constant regions, can also be used. Such antibodies can be produced using various techniques known in the art. For example in vitro methods involve use of recombinant libraries of human antibody fragments displayed on bacteriophage (e.g., Hoogenboom & Winter, (1991) J. Mol. Biol. 227: 381-8.) Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, (1988) Cold Spring Harbor Laboratory), but are not limited thereto. A protein A column and protein G column can be used as the affinity column. Exemplary protein A columns to be used include, for example, Hyper D, POROS and Sepharose F. F. (Pharmacia).

Exemplary chromatography, with the exception of affinity includes, for example, ion-exchange chromatography, hydrophobic chromatography, gel filtration, reverse-phase chromatography, adsorption chromatography and the like (Strategies for Protein Purification and Characterization: A Laboratory Course Manual. Ed Daniel R. Marshak et al., (1996) Cold Spring Harbor Laboratory Press). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a ZNFN3A1 polypeptide of the invention, by exposing an antibody of the invention to a sample presumed to contain a polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used. Cancer therapies directed at specific molecular alterations that occur in cancer cells have been validated through clinical development and regulatory approval of anti-cancer drugs such as trastuzamab (Herceptin) for the treatment of advanced BRC, imatinib mesylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F. et al., (2001) Clin Cancer Res.; 7(10): 2958-70. Review.; Slamon D J. et al., (2001) N Engl J Med.; 344(11): 783-92.; Rehwald U. et al., (2003) Blood.; 101(2): 420-4.; Fang G. et al., (2000). Blood, 96, 2246-53.). These drugs are clinically effective and better tolerated than traditional anti-cancer agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L. (2002). Oncology, 63 Suppl 1, 47-56.; Klejman A. et al., (2002) Oncogene, 21, 5868-76.). Therefore, future cancer treatments will probably involve combining conventional drugs with target-specific agents aimed at different characteristics of tumor cells such as angiogenesis and invasiveness.

These modulatory methods can be performed ex vivo or in vitro (e.g., by culturing the cell with the agent) or, alternatively, in vivo (e.g., by administering the agent to a subject). The methods involve administering a protein or combination of proteins or a nucleic acid molecule or combination of nucleic acid molecules as therapy to counteract aberrant expression of the differentially expressed genes or aberrant activity of their gene products.

Diseases and disorders that are characterized by increased (relative to a subject not suffering from the disease or disorder) expression levels or biological activities of genes and gene products, respectively, may be treated with therapeutics that antagonize (i.e., reduce or inhibit) activity of the over-expressed gene or genes. Therapeutics that antagonize activity can be administered therapeutically or prophylactically.

Accordingly, therapeutics that may be utilized in the context of the present invention include, e.g., (i) antibodies to the over-expressed gene or gene products; (ii) antisense nucleic acids or nucleic acids that are "dysfunctional" (i.e., due to a heterologous insertion within the nucleic acids of over-expressed gene); (iii) small interfering RNA (siRNA); or (iv) modulators (i.e., inhibitors, antagonists that alter the interaction between an over-expressed polypeptide and its binding partner). The dysfunctional antisense molecules are utilized to "knockout" endogenous function of a polypeptide by homologous recombination (see, e.g., Capecchi M R, (1989) Science 244: 1288-92.).

Increased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease, such that a disease or disorder is prevented or, alternatively, delayed in its progression.

Therapeutic methods of the present invention may include the step of contacting a cell with an agent that modulates one or more of the activities of the gene products of the differentially expressed gene. Examples of agent that modulates protein activity include, but are not limited to, nucleic acids, proteins, naturally-occurring cognate ligands of such proteins, peptides, peptidomimetics, and other small molecule.

Vaccinating Against BRC:

The present invention also relates to a method of treating or preventing BRC in a subject comprising the step of administering to said subject a vaccine comprising a polypeptide encoded by a nucleic acid of ZNFN3A1, an immunologically active fragment of said polypeptide, or a polynucleotide encoding such a polypeptide or fragment thereof. Administration of the polypeptide induces an anti-tumor immunity in a subject. To induce anti-tumor immunity, a polypeptide encoded by a nucleic acid of ZNFN3A1 an immunologically active fragment of said polypeptide, or a polynucleotide encoding such a polypeptide or fragment thereof is administered to subject in need thereof. Furthermore, the polypeptide encoded by a nucleic acid of ZNFN3A1 may induce antitumor immunity against invasion of BRC and IDC, respectively. The polypeptide or the immunologically active fragments thereof are useful as vaccines against BRC. In some cases, the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, a vaccine against BRC refers to a substance that has the ability to induce anti-tumor immunity upon inoculation into animals. According to the present invention, polypeptides encoded by ZNFN3A1 or fragments thereof, were suggested to be HLA-A24 or HLA-A*0201 restricted epitopes peptides that may induce potent and specific immune response against BRC cells expressing ZNFN3A1. Thus, the present invention also encompasses a method of inducing anti-tumor immunity using the polypeptides. In general, anti-tumor immunity includes immune responses such as follows:

induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is determined to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. Specifically, a foreign substance that enters the living body is presented to T cells and B cells by the action of antigen presenting cells (APCs). T cells that respond to the antigen presented by the APCs in an antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell via an APC, and detecting the induction of CTLs. Furthermore, APCs have the effect of activating CD4+ T cells, CD8+ T cells, macrophages, eosinophils, and NK cells. Since CD4+ T cells and CD8+ T cells are also important in anti-tumor immunity, the anti-tumor immunity-inducing action of the peptide can be evaluated using the activation effect of these cells as indicators.

A method for evaluating the inducing action of CTLs using dendritic cells (DCs) as the APC is well known in the art. DCs are a representative APCs having the strongest CTL-inducing action among APCs. In this method, the test polypeptide is initially contacted with DCs, and then the DCs are contacted with T cells. Detection of T cells having cytotoxic effects against the cells of interest after the contact with DC shows that the test polypeptide has an activity of inducing the cytotoxic T cells. Activity of CTLs against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DCs, peripheral blood mononuclear cells (PBMCs) may also be used as the APC. The induction of CTLs has been reported to be enhanced by culturing PBMCs in the presence of GM-CSF and IL-4. Similarly, CTLs have been shown to be induced by culturing PBMCs in the presence of keyhole limpet hemocyanin (KLH) and IL-7.

Test polypeptides confirmed to possess CTL-inducing activity by these methods are deemed to be polypeptides having DC activation effect and subsequent CTL-inducing activity. Therefore, polypeptides that induce CTLs against tumor cells are useful as vaccines against tumors. Furthermore, APCs that have acquired the ability to induce CTLs against tumors through contact with the polypeptides are also useful as vaccines against tumors. Furthermore, CTLs that have acquired cytotoxicity due to presentation of the polypeptide antigens by APCs can be also used as vaccines against tumors. Such therapeutic methods for tumors, using anti-tumor immunity due to APCs and CTLs, are referred to as cellular immunotherapy.

Generally, when using a polypeptide for cellular immunotherapy, efficiency of the CTL-induction is known to be increased by combining a plurality of polypeptides having different structures and contacting them with DCs. Therefore, when stimulating DCs with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide is deemed to have the ability to induce anti-tumor immunity.

Anti-tumor immunity is induced by administering the vaccine of this invention, and the induction of anti-tumor immunity enables treatment and prevention of BRC. Therapy against cancer or prevention of the onset of cancer includes any of the following steps, such as inhibition of the growth of cancerous cells, involution of cancer, and suppression of the occurrence of cancer. A decrease in mortality and morbidity of individuals having cancer, decrease in the levels of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analysis.

The above-mentioned protein having immunological activity or a vector encoding such a protein may be combined with an adjuvant. An adjuvant refers to a compound that enhances the immune response against the protein when administered together (or successively) with the protein having immunological activity. Exemplary adjuvants include, but are not limited to, cholera toxin, salmonella toxin, alum, and such. Furthermore, the vaccine of this invention may be combined appropriately with a pharmaceutically acceptable carrier. Examples of such carriers include, but are not limited to, sterilized water, physiological saline, phosphate buffer, culture fluid, and such. Furthermore, the vaccine may contain as necessary, stabilizers, suspensions, preservatives, surfactants, and such. The vaccine can be administered systemically or locally. Vaccine administration can be performed by single administration, or boosted by multiple administrations.

When using an APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APCs or CTLs, the cells may be administered to the subject. APCs can be also induced by introducing a vector encoding the polypeptide into PBMCs ex vivo. APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of a polypeptide of the present invention is provided. The pharmaceutical composition may be used for raising anti tumor immunity.

Pharmaceutical Compositions for Inhibiting BRC or Malignant BRC:

In the context of the present invention, suitable pharmaceutical formulations include those suitable for oral, rectal, nasal, topical (including buccal and sub-lingual), vaginal or parenteral (including intramuscular, sub-cutaneous and intravenous) administration, or for administration by inhalation or insufflation. Preferably, administration is intravenous. The formulations are optionally packaged in discrete dosage units. Pharmaceutical formulations suitable for oral administration include, but are not limited to, capsules, cachets or tablets, each containing a predetermined amount of active ingredient. Suitable formulations also include powders, granules, solutions, suspensions and emulsions. The active ingredient is optionally administered as a bolus electuary or paste. Tablets and capsules for oral administration may contain conventional excipients, such as binding agents, fillers, lubricants, disintegrant and/or wetting agents. A tablet may be made by compression or molding, optionally with one or more formulational ingredients. Compressed tablets may be prepared by compressing in a suitable machine the active ingredients in a free-flowing form, such as a powder or granules, optionally mixed with a binder, lubricant, inert diluent, lubricating, surface active and/or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives, such as suspending agents, emulsifying agents, non-aqueous vehicles (which may include edible oils), and/or preservatives. The tablets may optionally be formulated so as to provide slow or controlled release of the active ingredient therein. A package of tablets may contain one tablet to be taken on each of the month.

Formulations suitable for parenteral administration include, but are not limited to, aqueous and non-aqueous sterile injection solutions, optionally containing, for example, anti-oxidants, buffers, bacteriostats and solutes which render the formulation isotonic with the blood of the intended recipient; as well as aqueous and non-aqueous sterile suspensions including suspending agents and/or thickening agents. The formulations may be presented in unit dose or multi-dose containers, for example as sealed ampoules and vials, and may be stored in a freeze-dried (lyophilized) condition, requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations suitable for rectal administration include suppositories with standard carriers such as cocoa butter or polyethylene glycol. Formulations suitable for topical administration in the mouth, for example, buccally or sublingually, include, but are not limited to, lozenges, containing the active ingredient in a flavored base such as sucrose and acacia or tragacanth, and pastilles, comprising the active ingredient in a base such as gelatin and glycerin or sucrose and acacia. For intra-nasal administration, the compounds of the invention may be used as a liquid spray, a dispersible powder, or in the form of drops. Drops may be formulated with an aqueous or non-aqueous base also comprising one or more dispersing agents, solubilizing agents and/or suspending agents.

For administration by inhalation the compounds can be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichiorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base, such as lactose or starch. The powder composition may be presented in unit dosage form, for example, as capsules, cartridges, gelatin or blister packs, from which the powder may be administered with the aid of an inhalator or insufflators.

Other formulations include implantable devices and adhesive patches which release a therapeutic agent.

When desired, the above described formulations, adapted to give sustained release of the active ingredient, may be employed. The pharmaceutical compositions may also contain other active ingredients, such as antimicrobial agents, immunosuppressants and/or preservatives.

It should be understood that in addition to the ingredients particularly mentioned above, the formulations of this invention may include other agents conventional in the art with regard to the type of formulation in question. For example, formulations suitable for oral administration may include flavoring agents.

Preferred unit dosage formulations contain an effective dose, as recited below, or an appropriate fraction thereof, of the active ingredient.

For each of the aforementioned conditions, the compositions, e.g., polypeptides and organic compounds, can be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also the route of administration may vary depending upon the condition and its severity. In any event, appropriate and optimum dosages may be routinely calculated by those skilled in the art, taking into consideration the above-mentioned factors.

Aspects of the present invention are described in the following examples, which are not intended to limit the scope of the invention described in the claims. The following examples illustrate the identification and characterization of genes differentially expressed in BRC cells. However, methods and materials similar or equivalent to those described herein can be used in the practice or testing of the present invention.

Example 1

Enhanced ZNFN3A1 Expression in BRC

The global gene expression profile data obtained from 92 breast carcinomas using cDNA-microarray revealed that ZNFN3A1 expression was elevated in 36 of 69 invasive ductal carcinomas (IDC) and in 6 out of 11 ductal carcinoma in situ (DCIS), when the cut-off of tumor to normal tissue ratio was greater than two (FIG. 1a). This elevation was confirmed in 7 out of 12 IDCs selected randomly using cDNA that were used for microarray by semi-quantitative RT-PCR, compared to normal mammary ductal cells (FIG. 1b). To investigate ZNFN3A1 protein expression in BRC tissues, western blot analysis was carried out using protein extract from six bulk BRC tissues and their corresponding non-cancerous mammary tissues. A significant accumulation of ZNFN3A1 was consistently found in the six tumor tissues (FIG. 1c).

Figure 2:
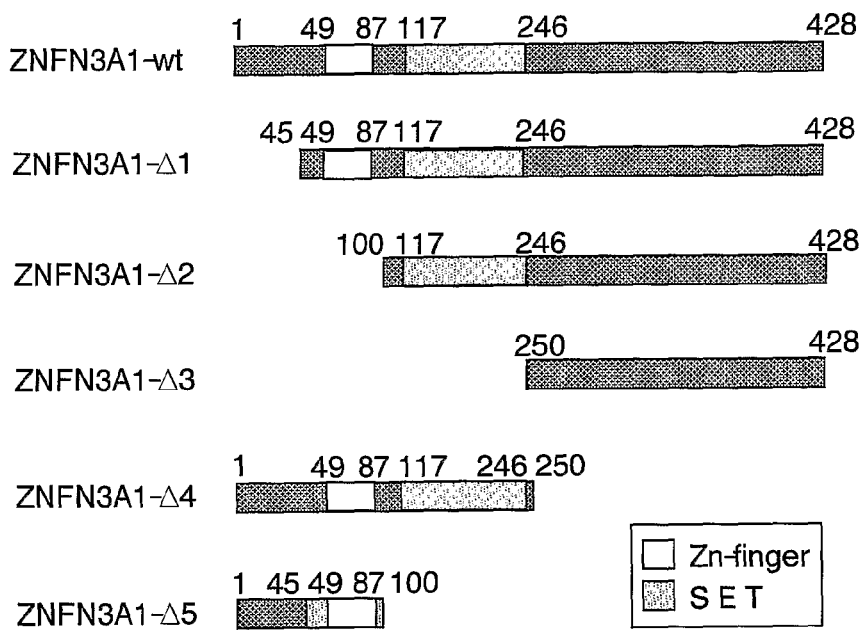
FIG. 2 depicts the cleaved form of the ZNFN3A1 protein in cells. Part (a) is a schematic presentation of plasmids expressing wild type and deleted forms of ZNFN3A1. Part (b) depicts the results of western blot analysis of wild type and mutant ZNFN3A1 using an anti-ZNFN3A1 (left panel) or anti-Flag (right panel) antibody.
Figure 2:
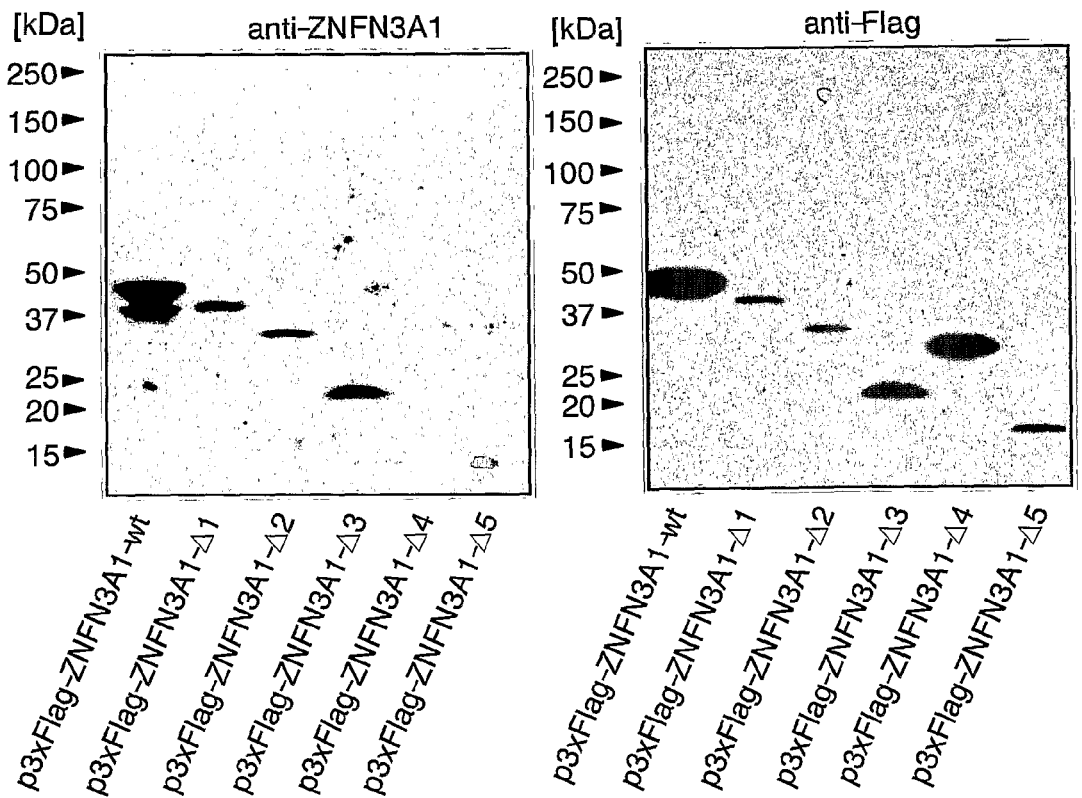

Since all western blot analyses of ZNFN3A1 protein detected two bands at 43 and 45 kDa in size (FIG. 1c), the two forms of protein were further investigated. Phosphatase treatment of the extracts did not change the intensity of both bands (data not shown). Interestingly, western blot analysis using extract from cells transfected with wild type plasmids showed two bands with anti-ZNFN3A1 antibody (FIG. 2b, left panel, lane 1), but did single 45-kDa band with anti-Flag antibody (FIG. 2b, right panel, lane 1). Since the plasmid expressed wild-type ZNFN3A1 that was fused with Flag-tag at its amino acid terminus, it was postulated that the lower band might be a cleaved form of ZNFN3A1 protein. Therefore, ZNFN3A1 plasmids were prepared expressing various deleted forms of ZNFN3A1 (FIG. 2a) and examined the mutant forms of protein by western blot analysis. The deletion mutants that did not contain the amino acid terminus (p3xFlag-ZNFN3A1-Δ1, -Δ2, and -Δ3) showed single band with anti-ZNFN3A1 antibody (FIG. 2b, left panel). This data is consistent with the view that the 43-kDa form of ZNFN3A results form cleavage between codons 1 and 45. Additionally, since the anti-ZNFN3A1 antibody did not detect any bands corresponding to C-terminal deleted forms of mutant ZNFN3A1 protein (p3xFlag-ZNFN3A1-Δ4 and -Δ5) (FIG. 2b left panel), the antibody should recognize an epitope(s) between codons 250 and 428.

Figure 3:
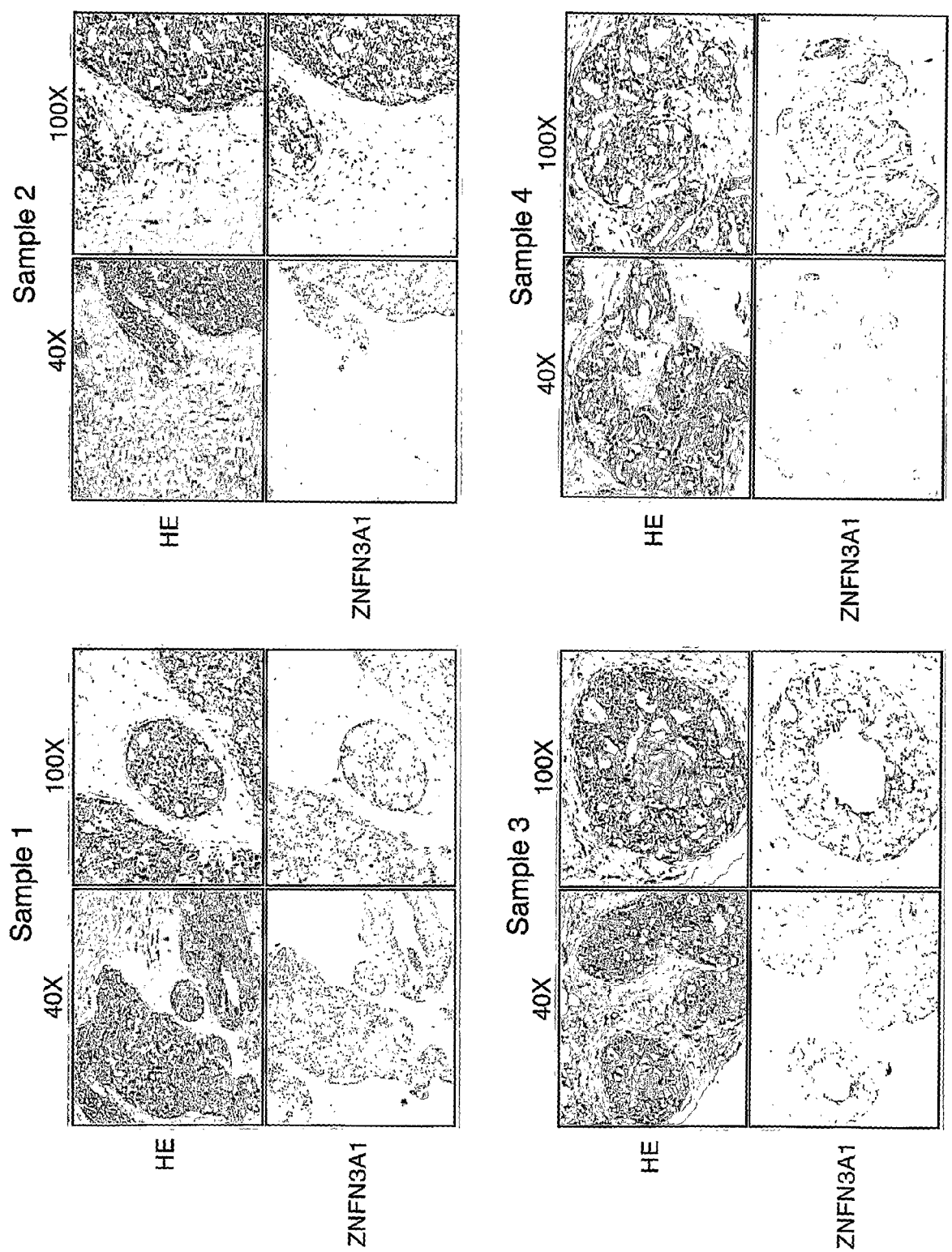
FIG. 3 depicts the results of immunohistochemical staining of the ZNFN3A1 protein in four BRC tissues. Frozen sections were stained with H&E (upper panels), and an anti-ZNFN3A1 antibody (lower panels).

Immunohistochemical staining of ZNFN3A1 using the antibody detected strong staining in breast carcinoma cells but not in stromal cells in the four cancer tissues examined (FIG. 3).

Example 2

Growth Suppression of BRC Cells by ZNFN3A1 siRNA

To test whether suppression of ZNFN3A1 may result in the induction of apoptosis in BRC cells, a cell viability assay was carried out using the ZNFN3A1 siRNA-12 that effectively suppressed ZNFN3A1 expression in colon and liver carcinoma cells (see WO2004/076623, the entire contents of which is incorporated by reference herein). The oligonucleotides used for construction cZNFN3A1 siRNA expression vector (for target sequence of SEQ ID NO: 1) are as follows: psiU6BX-ZNFN3A1-12, Forward: 5'-AACATCTAC-CAGCTGAAGGTGTTCAAGAGAC ACCTTCAGCTGG-TAGATGTT-3' (SEQ ID NO; 2), Reverse: 5'-AACATCTACCAGCTGAAGGTGTCTCT-TGAACACCTTCAGCTGGTAG ATGTT-3¹ (SEQ ID NO; 3).

Figure 4:
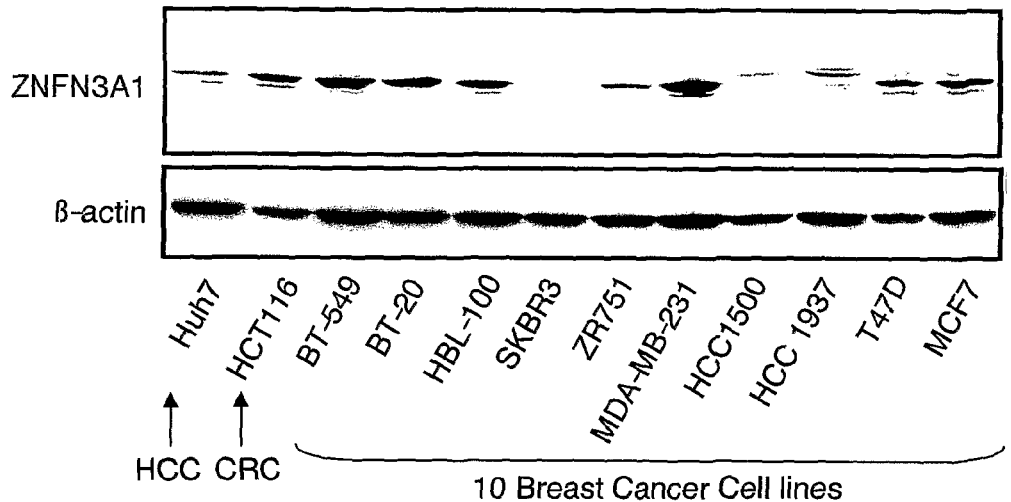
FIG. 4 depicts the involvement of ZNFN3A1 in the growth of BRC cells. Part (a) depicts ZNFN3A1 expression in BRC cell lines. Part (b) depicts the knockdown effect of ZNFN3A1 on the growth of BRC cells. In particular, ZNFN3A1-siRNA#12(si#12) significantly suppressed their growth as compared to mock or Luciferase-siRNA (siLuc).
Figure 4:
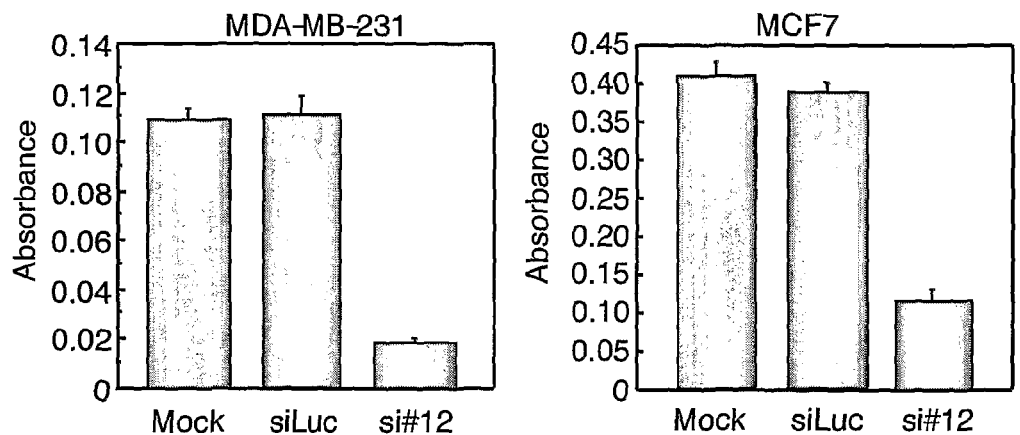
Figure 4:
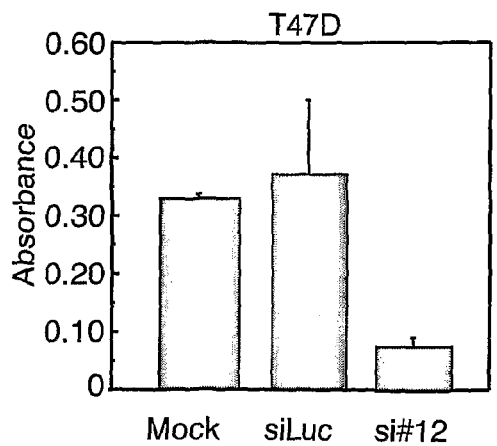

Western blot analysis of ten BRC cell lines revealed that ZNFN3A1 was abundantly expressed in 8 out of 10 BRC cells such as BT-20, HBL-100, MDA-MB-231, MCF7 and T47D cells (FIG. 4a). MDA-MB-231, MCF7 and T47D cells were transfected with psiU6BX-ZNFN3A1-12, psiU6-Luciferase, or psiU6 (mock), cultured them with appropriate concentration of G418, and analyzed cell viability by cell counting kit. As a result, psiU6BX-ZNFN3A1-12 showed significant growth inhibitory effect compared to psiU6BX-Luciferase or psiU6BX-mock in the three cell lines (FIG. 4b). Therefore, inhibition of ZNFN3A1 appears to be a rational strategy to treat BRC.

INDUSTRIAL APPLICABILITY

The gene-expression analysis of BRC described herein, obtained through a combination of laser-capture dissection and genome-wide cDNA microarray, has identified a specific gene, ZNFN3A1, as a target for cancer prevention and therapy. Based on the expression of this differentially expressed gene, the present invention provides molecular diagnostic markers for identifying and detecting BRC.

The methods described herein are also useful in the identification of additional molecular targets for prevention, diagnosis and treatment of BRC. The data reported herein add to a comprehensive understanding of BRC, facilitate development of novel diagnostic strategies, and provide clues for identification of molecular targets for therapeutic drugs and preventative agents. Such information contributes to a more profound understanding of breast tumorigenesis, and provide indicators for developing novel strategies for diagnosis, treatment, and ultimately prevention of BRC.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method of diagnosing breast cancer or a predisposition for developing breast cancer in a subject, comprising determining a level of expression of ZNFN3A1 in a patient-derived biological sample, wherein an increase in said sample expression level as compared to a normal control level of said gene indicates that said subject suffers from or is at risk of developing breast cancer, wherein said patient-derived biological sample comprises a cell obtained from breast tissue.

2. The method of claim 1, wherein said sample expression level is at least 10% greater than said normal control level.

3. The method of claim 1, wherein gene expression level is determined by a method selected from the group consisting of:

(a) detecting mRNA of ZNFN3A1,
(b) detecting a protein encoded by ZNFN3A1, and
(c) detecting a biological activity of a protein encoded by ZNFN3A1.

4. The method of claim 1, wherein said patient-derived biological sample comprises an epithelial cell obtained from breast tissue.

5. The method of claim 1, wherein said patient-derived biological sample comprises a breast cancer cell.

6. The method of claim 1, wherein said patient-derived biological sample comprises an epithelial cell from a breast cancer cell.

7. The method of claim 1, wherein said breast cancer is breast ductal carcinoma.

* * * * *

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial
<220> FEATURE:
<223> OTHER INFORMATION: An artificially synthesized target sequence for
      siRNA

<400> SEQUENCE: 1
aacatctacc agctgaaggt g                                                  21

<210> SEQ ID NO 2
<211> LENGTH: 51
<212> TYPE: DNA
<213> ORGANISM: Artificial
<220> FEATURE:
<223> OTHER INFORMATION: An artificially synthesized origonucleotide
      sequence for siRNA

<400> SEQUENCE: 2
aacatctacc agctgaaggt gttcaagaga caccttcagc tggtagatgt t                 51

<210> SEQ ID NO 3
<211> LENGTH: 51
<212> TYPE: DNA
<213> ORGANISM: Artificial
<220> FEATURE:
<223> OTHER INFORMATION: An artificially synthesized origonucleotide
      sequence for siRNA

<400> SEQUENCE: 3
aacatctacc agctgaaggt gtctcttgaa caccttcagc tggtagatgt t                 51

<210> SEQ ID NO 4
<211> LENGTH: 1622
<212> TYPE: DNA
<213> ORGANISM: Homo sapiens
<220> FEATURE:
<221> NAME/KEY: CDS
```

<222> LOCATION: (96)..(1382)

<400> SEQUENCE: 4

```
gtgcgcgcag ggcgcaggcg cgcgggtccc ggcagcccgt gagacgcccg ctgctggacg      60
cgggtagccg tctgaggtgc cggagctgcg ggagg atg gag ccg ctg aag gtg        113
                                       Met Glu Pro Leu Lys Val
                                        1               5 gaa aag ttc gca acc gcc aac agg gga aac ggg ctg cgc gcc gtg acc       161
Glu Lys Phe Ala Thr Ala Asn Arg Gly Asn Gly Leu Arg Ala Val Thr
             10                  15                  20 ccg ctg cgc ccc gga gag cta ctc ttc cgc tcg gat ccc ttg gcg tac       209
Pro Leu Arg Pro Gly Glu Leu Leu Phe Arg Ser Asp Pro Leu Ala Tyr
         25                  30                  35 acg gtg tgc aag ggg agt cgt ggc gtc gtc tgc gac cgc tgc ctt ctc       257
Thr Val Cys Lys Gly Ser Arg Gly Val Val Cys Asp Arg Cys Leu Leu
     40                  45                  50 ggg aag gaa aag ctg atg cga tgc tct cag tgc cgc gtc gcc aaa tac       305
Gly Lys Glu Lys Leu Met Arg Cys Ser Gln Cys Arg Val Ala Lys Tyr
 55                  60                  65                  70 tgt agt gct aag tgt cag aaa aaa gct tgg cca gac cac aag cgg gaa       353
Cys Ser Ala Lys Cys Gln Lys Lys Ala Trp Pro Asp His Lys Arg Glu
                 75                  80                  85 tgc aaa tgc ctt aaa agc tgc aaa ccc aga tat cct cca gac tcc gtt       401
Cys Lys Cys Leu Lys Ser Cys Lys Pro Arg Tyr Pro Pro Asp Ser Val
             90                  95                 100 cga ctt ctt ggc aga gtt gtc ttc aaa ctt atg gat gga gca cct tca       449
Arg Leu Leu Gly Arg Val Val Phe Lys Leu Met Asp Gly Ala Pro Ser
        105                 110                 115 gaa tca gag aag ctt tac tca ttt tat gat ctg gag tca aat att aac       497
Glu Ser Glu Lys Leu Tyr Ser Phe Tyr Asp Leu Glu Ser Asn Ile Asn
    120                 125                 130 aaa ctg act gaa gat aag aaa gag ggc ctc agg caa ctc gta atg aca       545
Lys Leu Thr Glu Asp Lys Lys Glu Gly Leu Arg Gln Leu Val Met Thr
135                 140                 145                 150 ttt caa cat ttc atg aga gaa gaa ata cag gat gcc tct cag ctg cca       593
Phe Gln His Phe Met Arg Glu Glu Ile Gln Asp Ala Ser Gln Leu Pro
                155                 160                 165 cct gcc ttt gac ctt ttt gaa gcc ttt gca aaa gtg atc tgc aac tct       641
Pro Ala Phe Asp Leu Phe Glu Ala Phe Ala Lys Val Ile Cys Asn Ser
            170                 175                 180 ttc acc atc tgt aat gcg gag atg cag gaa gtt ggt gtt ggc tta tat       689
Phe Thr Ile Cys Asn Ala Glu Met Gln Glu Val Gly Val Gly Leu Tyr
        185                 190                 195 ccc agt atc tct ttg ctc aat cac agc tgt gac ccc aac tgt tcg att       737
Pro Ser Ile Ser Leu Leu Asn His Ser Cys Asp Pro Asn Cys Ser Ile
    200                 205                 210 gtg ttc aat ggg ccc cac ctc tta ctg cga gca gtc cga gac atc gag       785
Val Phe Asn Gly Pro His Leu Leu Leu Arg Ala Val Arg Asp Ile Glu
215                 220                 225                 230 gtg gga gag gag ctc acc atc tgc tac ctg gat atg ctg atg acc agt       833
Val Gly Glu Glu Leu Thr Ile Cys Tyr Leu Asp Met Leu Met Thr Ser
                235                 240                 245 gag gag cgc cgg aag cag ctg agg gac cag tac tgc ttt gaa tgt gac       881
Glu Glu Arg Arg Lys Gln Leu Arg Asp Gln Tyr Cys Phe Glu Cys Asp
            250                 255                 260 tgt ttc cgt tgc caa acc cag gac aag gat gct gat atg cta act ggt       929
Cys Phe Arg Cys Gln Thr Gln Asp Lys Asp Ala Asp Met Leu Thr Gly
        265                 270                 275 gat gag caa gta tgg aag gaa gtt caa gaa tcc ctg aaa aaa att gaa       977
Asp Glu Gln Val Trp Lys Glu Val Gln Glu Ser Leu Lys Lys Ile Glu
```

```
                280                 285                 290
gaa ctg aag gca cac tgg aag tgg gag cag gtt ctg gcc atg tgc cag         1025
Glu Leu Lys Ala His Trp Lys Trp Glu Gln Val Leu Ala Met Cys Gln
295                 300                 305                 310 gca atc ata agc agc aat tct gaa cgg ctt ccc gat atc aac atc tac         1073
Ala Ile Ile Ser Ser Asn Ser Glu Arg Leu Pro Asp Ile Asn Ile Tyr
                315                 320                 325 cag ctg aag gtg ctc gac tgc gcc atg gat gcc tgc atc aac ctc ggc         1121
Gln Leu Lys Val Leu Asp Cys Ala Met Asp Ala Cys Ile Asn Leu Gly
            330                 335                 340 ctg ttg gag gaa gcc ttg ttc tat ggt act cgg acc atg gag cca tac         1169
Leu Leu Glu Glu Ala Leu Phe Tyr Gly Thr Arg Thr Met Glu Pro Tyr
        345                 350                 355 agg att ttt ttc cca gga agc cat ccc gtc aga ggg gtt caa gtg atg         1217
Arg Ile Phe Phe Pro Gly Ser His Pro Val Arg Gly Val Gln Val Met
    360                 365                 370 aaa gtt ggc aaa ctg cag cta cat caa ggc atg ttt ccc caa gca atg         1265
Lys Val Gly Lys Leu Gln Leu His Gln Gly Met Phe Pro Gln Ala Met
375                 380                 385                 390 aag aat ctg aga ctg gct ttt gat att atg aga gtg aca cat ggc aga         1313
Lys Asn Leu Arg Leu Ala Phe Asp Ile Met Arg Val Thr His Gly Arg
                395                 400                 405 gaa cac agc ctg att gaa gat ttg att cta ctt tta gaa gaa tgc gac         1361
Glu His Ser Leu Ile Glu Asp Leu Ile Leu Leu Leu Glu Glu Cys Asp
            410                 415                 420 gcc aac atc aga gca tcc taa gggaacgcag tcagagggaa atacggcgtg            1412
Ala Asn Ile Arg Ala Ser
        425 tgtctttgtt gaatgcctta ttgaggtcac acactctatg ctttgttagc tgtgtgaacc      1472 tctcctattg gaaattctgt tccgtgtttg tgtaggtaaa taaaggcaga catggtttgc      1532 aaaccacaag aatcattagt tgtagagaag cacgattata ataaattcaa acatttggt      1592 tgaggatgcc aaaaaaaaaa aaaaaaaaaa                                        1622

<210> SEQ ID NO 5
<211> LENGTH: 428
<212> TYPE: PRT
<213> ORGANISM: Homo sapiens

<400> SEQUENCE: 5

Met Glu Pro Leu Lys Val Glu Lys Phe Ala Thr Ala Asn Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
    130                 135                 140
```

-continued

```
Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
    210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
            260                 265                 270

Ala Asp Met Leu Thr Gly Asp Glu Gln Val Trp Lys Glu Val Gln Glu
        275                 280                 285

Ser Leu Lys Lys Ile Glu Glu Leu Lys Ala His Trp Lys Trp Glu Gln
    290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
            340                 345                 350

Arg Thr Met Glu Pro Tyr Arg Ile Phe Phe Pro Gly Ser His Pro Val
        355                 360                 365

Arg Gly Val Gln Val Met Lys Val Gly Lys Leu Gln Leu His Gln Gly
    370                 375                 380

Met Phe Pro Gln Ala Met Lys Asn Leu Arg Leu Ala Phe Asp Ile Met
385                 390                 395                 400

Arg Val Thr His Gly Arg Glu His Ser Leu Ile Glu Asp Leu Ile Leu
                405                 410                 415

Leu Leu Glu Glu Cys Asp Ala Asn Ile Arg Ala Ser
            420                 425
```